United States Patent
Ohrn et al.

(10) Patent No.: US 10,168,885 B2
(45) Date of Patent: Jan. 1, 2019

(54) SYSTEMS AND METHODS FOR MAKING TWO DIMENSIONAL GRAPHS OF COMPLEX MOLECULES

(71) Applicant: ZYMEWORKS INC., Vancouver (CA)

(72) Inventors: Anders Ohrn, Toronto (CA); Scott Paul MacDonald, Delta (CA)

(73) Assignee: ZYMEWORKS INC., Vancouver (CA)

( * ) Notice: Subject to any disclaimer, the term of this patent is extended or adjusted under 35 U.S.C. 154(b) by 140 days.

(21) Appl. No.: 15/023,532

(22) PCT Filed: Sep. 17, 2014

(86) PCT No.: PCT/CA2014/050885
§ 371 (c)(1),
(2) Date: Mar. 21, 2016

(87) PCT Pub. No.: WO2015/042699
PCT Pub. Date: Apr. 2, 2015

(65) Prior Publication Data
US 2016/0210767 A1 Jul. 21, 2016

Related U.S. Application Data

(60) Provisional application No. 61/882,531, filed on Sep. 25, 2013.

(51) Int. Cl.
*G06T 11/20* (2006.01)
*G06F 3/0484* (2013.01)
(Continued)

(52) U.S. Cl.
CPC .......... *G06F 3/04847* (2013.01); *G06F 19/70* (2013.01); *G06T 15/10* (2013.01)

(58) Field of Classification Search
CPC ...... G06F 3/04847; G06F 19/70; G06T 15/10
See application file for complete search history.

(56) References Cited

U.S. PATENT DOCUMENTS

| 5,386,507 A | 1/1995 | Teig et al. |
| 6,125,234 A | 9/2000 | De Jenlis |

(Continued)

FOREIGN PATENT DOCUMENTS

| EP | 1939779 A2 | 7/2008 |
| WO | WO 1999/01744 A1 | 1/1999 |

(Continued)

OTHER PUBLICATIONS

Berinde, V. "On Some Exit Criteria for the Newton Method." *Novi Sad J. Math.*, vol. 27, No. 1, pp. 19-26, Department of Mathematics, University of Baia Mare, Romania (1997).

(Continued)

*Primary Examiner* — Barry Drennan
*Assistant Examiner* — Terrell Robinson
(74) *Attorney, Agent, or Firm* — Morgan, Lewis & Bockius LLP; Brett Lovejoy

(57) ABSTRACT

Systems and methods for visualization of a molecule, comprising a set of particles, are provided. A set of three-dimensional coordinates is obtained, each coordinate describing a position for a corresponding particle. A cost function containing an error in a set of two-dimensional coordinates, where each two-dimensional coordinate corresponds to a three-dimensional coordinate in the set of three-dimensional coordinates, is minimized until an exit condition is achieved. The minimization alters the two-dimensional coordinate values. A set of physical properties $S_M$ is obtained, each such property representing a property shared by a pair of particles in the molecule. The coordinates are plotted as nodes of a two-dimensional graph after minimization, connected by a plurality of edges. An edge connects a coordinate pair in the graph that corresponds to a pair of particles in the molecule. A characteristic of the (Continued)

edge is determined by a physical property for the pair of particles.

30 Claims, 17 Drawing Sheets

(51) Int. Cl.
*G06F 19/00* (2018.01)
*G06T 15/10* (2011.01)

(56) References Cited

U.S. PATENT DOCUMENTS

| 6,675,103 | B1 | 1/2004 | Patterson |
| 7,188,055 | B2 | 3/2007 | Agrafiotis et al. |
| 7,912,689 | B1 | 3/2011 | Helson |
| 2004/0088116 | A1 | 5/2004 | Khalil et al. |
| 2004/0088118 | A1* | 5/2004 | Jensen .................. G06F 19/708 702/30 |
| 2007/0143030 | A1 | 6/2007 | Clark et al. |
| 2008/0234996 | A1 | 9/2008 | Ghosh et al. |
| 2012/0154440 | A1 | 6/2012 | Nicholls et al. |
| 2015/0051889 | A1 | 2/2015 | Ohrn |

FOREIGN PATENT DOCUMENTS

| WO | WO 2010/000268 | 1/2010 |
| WO | WO 2011/047684 | 4/2011 |
| WO | WO 2013/138923 | 9/2013 |

OTHER PUBLICATIONS

Brocchieri, L. and Karlin, S., "Geometry of interplanar residue contacts in protein structures." *Proc. Natl. Acad. Sci. USA*, vol. 91, pp. 9297-9301 (1994).
Chin, J.W. et al., "Progress Toward an Expanded Eukaryotic Genetic Code." *Chemistry & Biology*, vol. 10, pp. 511-519 (2003).
Chin, J.W. et al., "An Expanded Eukaryotic Genetic Code." *Science*, vol. 301, pp. 964-967 (2003).
Jenkins, A.D. et al., "Glossary of Basic Terms in Polymer Science." *Pure & Appl. Chem.*, vol. 68, No. 12, pp. 2287-2311 (1996).
Simon, R. J. et al., "Peptoids: A modular approach to drug discovery." *Proc. Natl. Acad. Sci., USA*, vol. 89, pp. 9367-9371 (1992).

* cited by examiner

SYSTEMS AND METHODS FOR MAKING TWO DIMENSIONAL GRAPHS OF COMPLEX MOLECULES

CROSS REFERENCE TO RELATED APPLICATION

This application claims the benefit of U.S. Provisional Application No. 61/882,531 filed Sep. 25, 2013, which is hereby incorporated by reference herein in its entirety.

This application is related to U.S. Provisional Application No. 61/613,711, filed Mar. 21, 2012, which is hereby incorporated by reference herein in its entirety.

This application is also related to PCT International Application No. PCT/CA2013/050183, filed Mar. 12, 2013, which is hereby incorporated by reference herein in its entirety.

TECHNICAL FIELD

The disclosed embodiments relate generally to systems and methods for visualizing complex molecules, such as polymers (e.g., proteins, nucleic acids, ribonucleic acids, polysaccharides, etc.), dendimers, organometallic complexes, surfactant self-assemblies and complex fullerenes in two dimensions.

BACKGROUND

In many applications, such as macromolecular structural studies, drug discovery, diagnostic development, detergent design, polymer chemistry, polymer physics, and polymer science, large volumes of physical data are acquired relating to (i) the physical properties of residues of complex molecules and (ii) physical properties shared between discrete groups of atoms, such as residues, in such complex molecules. Examples of the former physical properties include, but are not limited to, accessible surface area, solvent-excluded surface area, electrical charge, hydrophobicity, hydrophilicity, polarity, aromaticity, molecular weight and volume. Examples of the latter include physical properties include, but are not limited to, hydrogen bonds, close hydrogen bonds, carbon-carbon contacts, carbon-nitrogen contacts, carbon-oxygen contacts, carbon-sulfur contacts, π-π interactions, and π-cation interactions.

Moreover, complex molecules typically have many discrete groups of atoms, termed particles herein, and adopt unique complex three-dimensional conformations. This makes visualization of the above-identified physical data challenging. Thus, given the above background, what is needed in the art are improved systems and methods for visualizing relational data associated with the physical properties of particles of complex molecules.

SUMMARY

Systems and methods for two-dimensional visualization of a complex molecule that address the shortcomings of the prior art are provided. In the present disclosure, the three-dimensional coordinates of the complex molecule are compressed into a two-dimensional graph with minimized loss in structural fidelity. The two-dimensional graph comprises nodes and edges. Each node corresponds to a part of the complex molecule. Edges between respective node pairs correspond to a physical property shared by the respective node pairs. More specifically, a characteristic of an edge between a pair of nodes is determined by a property shared by the portions of the complex molecule represented by the pair of nodes. For instance, if the pair of nodes represent portions of the complex molecule that are covalently bound to each other, the edge may be drawn as a thick dark line. Here, the characteristic then is the fact that the edge is drawn in this manner. In some embodiments, the complex molecule macromolecule comprising a nucleic acid or a protein and each node represents a residue in the macromolecule. In some embodiments, a characteristic of each node in the graph is determined by a physical property of the portion of the macromolecule that the node represents. For instance, in some embodiments, the physical property is hydrophobicity, with the nodes for more hydrophobic particles within the complex molecule being drawn larger than the nodes for more hydrophilic particles within the complex molecule. The disclosed systems and methods for making graphs produce graphs that are highly advantageous because they allow for the visualization of physical properties of complex molecules in two dimensions.

In one aspect, the present disclosure provides systems and methods for two-dimensional visualization of a complex molecule. The complex molecule comprises a set of particles $\{p_1, \ldots, p_N\}$. For instance, in some embodiments, each particle is a residue. In one particular example, the complex molecule is a protein and each particle in the set of particles is an amino acid residue of the protein. A set of N three-dimensional coordinates $\{x_1, \ldots, x_N\}$ is obtained, each $x_i$ in $\{x_1, \ldots, x_N\}$ describing a three-dimensional position for a corresponding particle $p_i$ in $\{p_1, \ldots, p_N\}$. In typical embodiments, there is only one coordinate for each particle, although more than one coordinate is possible. It will be appreciated that each particle may comprise several covalently bound atoms and thus may have several coordinates, for instance, one for each atom. In some such embodiments, a single coordinate is selected for each particle. In the case of proteins in accordance with some embodiments, the coordinate of the $C_\alpha$ carbon is selected. In some embodiments, the coordinate that represents the center of mass of the particle is selected to represent the particle in the set of N three-dimensional coordinates $\{x_1, \ldots, x_N\}$. It will be appreciated that the three-dimensional coordinates of the macromolecule may be in any reference frame so long as each particle is in the same reference frame.

In accordance with the systems and methods of the present disclosure, a cost function containing the error in the set of two-dimensional coordinates $(c_1, \ldots, c_N)$ is constructed. Each $c_i$ in $(c_1, \ldots, c_N)$ corresponds to a three-dimensional coordinate $x_i$ in $\{x_1, \ldots, x_N\}$. The three-dimensional coordinates are used to devise an initial set of the two-dimensional coordinates using, for instance, a dimension reduction scheme such as linear principal component analysis. Using the initial set of the two-dimensional coordinates as a starting point, this cost function is then minimized until an exit condition is achieved. The minimization alters the values of $(c_1, \ldots, c_N)$ and produces a refined set of two-dimensional coordinates that reproduces the three-dimensional structural features of the complex molecule in two-dimensional space with a reduced loss of structural fidelity.

With the optimized two-dimensional coordinates in hand, it is possible to construct the two-dimensional graph. Each respective optimized coordinate $c_i$ in $(c_1, \ldots, c_N)$ uniquely corresponds to (i) a particle in the complex molecule and (ii) a node in the graph. Each respective edge in the graph is bounded by a pair of nodes. Each respective edge is drawn in the graph in a manner that represents a physical characteristic shared by the pair nodes that bounds the respective edge. To this end, a set of physical properties $S_M$ is obtained, each $s_{i,j}$ in $S_M$ representing a physical property shared by a pair of particles $(p_i, p_j)$ in $\{p_1, \ldots, p_N\}$.

Advantageously, in addition to representing physical properties shared by pairs of particles in the complex molecule, physical properties of the particles themselves may be represented in the graph. To this end, a second set of physical properties $K_M$ is obtained. Each physical property $k_i$ in $K_M$ represents a physical property of a corresponding particle $p_i$ in $\{p_1, \ldots, p_N T\}$. Then, a characteristic of a respective node in the plurality of nodes in the graph is determined by a value of or a type of the physical property of the corresponding particle $p_i$ in $K_M$.

BRIEF DESCRIPTION OF THE DRAWINGS

The embodiments disclosed herein are illustrated by way of example, and not by way of limitation, in the figures of the accompanying drawings. Like reference numerals refer to corresponding parts throughout the drawings.

DETAILED DESCRIPTION OF THE EMBODIMENTS

The embodiments described herein provide systems and methods for visualizing macromolecules in two dimensions.

Figure 1:
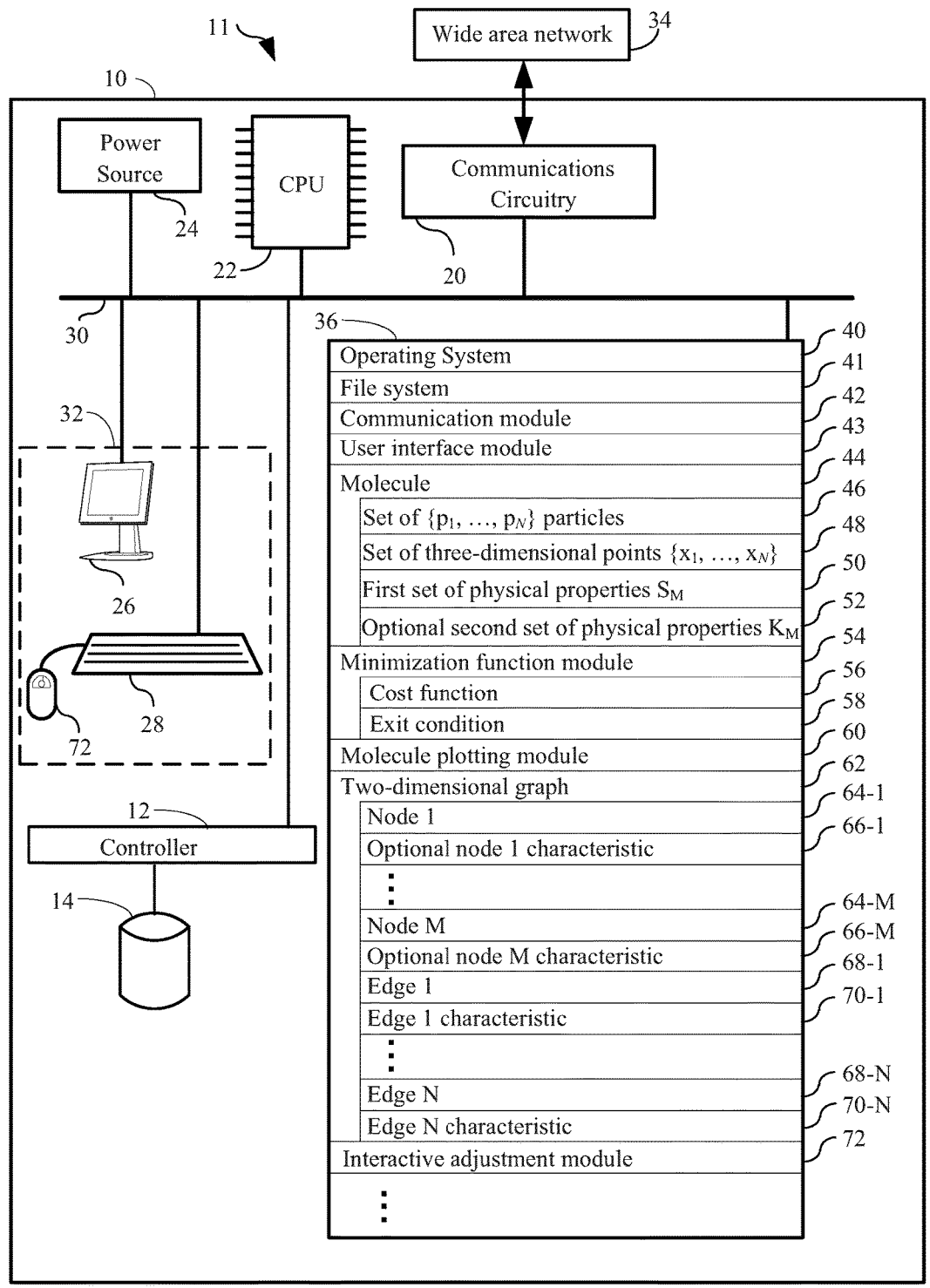
FIG. 1 is a block diagram illustrating a system, according to some embodiments.

FIG. 1 is a block diagram illustrating a computer according to some embodiments. The computer 10 typically includes one or more processing units (CPU's, sometimes called processors) 22 for executing programs (e.g., programs stored in memory 36), one or more network or other communications interfaces 20, memory 36, a user interface 32, which includes one or more input devices (such as a keyboard 28, mouse 72, touch screen, keypads, etc.) and one or more output devices such as a display device 26, one or more communication buses 30 for interconnecting these components, and a power source 24. The communication buses 30 may include circuitry (sometimes called a chipset) that interconnects and controls communications between system components.

Memory 36 includes high-speed random access memory, such as DRAM, SRAM, DDR RAM or other random access solid state memory devices; and typically includes non-volatile memory, such as one or more magnetic disk storage devices, optical disk storage devices, flash memory devices, or other non-volatile solid state storage devices. Memory 36 optionally includes one or more storage devices remotely located from the CPU(s) 22. Memory 36, or alternately the non-volatile memory device(s) within memory 36, comprises a non-transitory computer readable storage medium. In some embodiments, the non-volatile components in memory 36 include one or more hard drives 14 controlled by one or more hard drive controllers 12. In some embodiments, memory 36 or the computer readable storage medium of memory 36 stores the following programs, modules and data structures, or a subset thereof:

- an operating system 40 that includes procedures for handling various basic system services and for performing hardware dependent tasks;
- a file system 41 for handling basic file I/O tasks;
- an optional communication module 42 that is used for connecting the computer 10 to other computers via the one or more communication interfaces 20 (wired or wireless) and one or more communication networks 34, such as the Internet, other wide area networks, local area networks, metropolitan area networks, and so on;
- an optional user interface module 43 that receives commands from the user via the input devices 28, 72, etc. and generates user interface objects in the display device 26;
- molecule data 44 for a complex molecule that is to be visualized in two dimensions;
- a minimization function module 54 for minimizing a cost function 56 that represents the error a two dimensional coordinate set for the complex molecule incurs in representing a three dimensional coordinate set for the complex molecule to be visualized, as described herein, until an exit condition 58 is achieved;
- a molecule plotting module 60 for plotting the two-dimensional coordinates, after minimization, as a two-dimensional graph 62 comprising nodes 64 and edges 68, where each node 64 in the graph 62 represents a portion of the complex molecule 44 and a characteristic of each respective edge 68 in the graph is determined by a physical property of the portions of the complex molecule 44 represented by the nodes 64 bounding the respective edge 68; and
- an interactive adjustment module 72 for manually adjusting positions of nodes and/or edges in the two-dimensional graph.

In some embodiments, the complex molecule data 44 for the complex molecule of interest includes a set of $\{p_1, \ldots, p_N\}$ particles 46. Each particle $p_i$ in the set of $\{p_1, \ldots, p_N\}$ particles represents a different plurality of covalently bound atoms in the macromolecule. By plurality of covalently bound atoms in the complex molecule, it is meant that each atom in the plurality of atoms is covalently bound to at least one other atom in the plurality of atoms. This is the case, for instance, in some exemplary embodiments where the complex molecule is a protein or nucleic acid and each particle is one or more residue of the protein or nucleic acid. Thus, in some embodiments, each particle $p_i$ in the set of particles $\{p_1, \ldots, p_N\}$ is for a different residue in the macromolecule. For example, consider the case in which the macromolecule is a protein with three hundred residues. In this example, each of the three hundred residues would be a particle $p_i$ in the set of $\{p_1, \ldots, p_N\}$ particles.

In some embodiments, the complex molecule of interest comprises between 2 and 5,000 particles, between 20 and 50,000 particles, more than 30 particles, more than 50 particles, or more than 100 particles. In some embodiments, a particle $p_i$ in the set of particles $\{p_1, \ldots, p_N\}$ for the complex molecule of interest comprises two or more atoms, three or more atoms, four or more atoms, five or more atoms, six or more atoms, seven or more atoms, eight or more atoms, nine or more atoms or ten or more atoms. In some embodiments, each particle $p_i$ in the set of particles $\{p_1, \ldots, p_N\}$ for the complex molecule of interest comprises two or more atoms, three or more atoms, four or more atoms, five or more atoms, six or more atoms, seven or more atoms, eight or more atoms, nine or more atoms or ten or more atoms. In some embodiments the complex molecule of interest has a molecular weight of 100 Daltons or more, 200 Daltons or more, 300 Daltons or more, 500 Daltons or more, 1000 Daltons or more, 5000 Daltons or more, 10,000 Daltons or more, 50,000 Daltons or more or 100,000 Daltons or more.

Moreover, in some embodiments, complex molecule data 44 further comprises a set of N three-dimensional coordinates $\{x_1, \ldots, x_N\}$ 48, where each respective $x_i$ in $\{x_1, \ldots, x_N\}$ corresponds to a $p_i$ in $\{p_1, \ldots, p_N\}$ and represents the position of $p_i$ in three-dimensional space. For example, in some embodiments, the complex molecule is a protein, each $p_i$ in the set of $\{p_1, \ldots, p_N\}$ particles represents a residue in the protein, and each respective $x_i$ in $\{x_1, \ldots, x_N\}$ is the three-dimensional coordinates of the $C_\alpha$ carbon of the residue represented by the $p_i$ in the set of $\{p_1, \ldots, p_N\}$ particles that corresponds to the respective $x_i$. In other embodiments, each respective $x_i$ in $\{x_1, \ldots, x_N\}$ is the three-dimensional coordinates of the center of mass of the $p_i$ in the set of $\{p_1, \ldots, p_N\}$ particles. In some embodiments, the complex molecule is a protein, each $p_i$ in the set of $\{p_1, \ldots, p_N\}$ particles represents a residue in the protein, and each respective $x_i$ in $\{x_1, \ldots, x_N\}$ is the three-dimensional coordinates of a predetermined main chain atom (N, $C_a$, C, or O) of the residue represented by the $p_i$ in the set of $\{p_1, \ldots, p_N\}$ particles that corresponds to the respective $x_i$.

In some embodiments, complex molecule data 44 further comprises a first set of physical properties $S_M$ 50. Each physical property $s_{i,j}$ in $S_M$ represents a physical property shared by a corresponding pair of particles $(p_i, p_j)$ in $\{p_1, \ldots, p_N\}$. An example of such a physical properties represented by $s_{i,j}$ for the corresponding pair of particles $(p_i, p_j)$ in $\{p_1, \ldots, p_N\}$ is a presence of a covalent bond between a first atom in the plurality of atoms represented by particle $p_i$ and a second atom in the plurality of atoms represented by particle $p_j$.

In some embodiments, complex molecule data 44 further comprises a second set of physical properties $K_M$ 52. Each physical property $k_i$ in $K_M$ represents a physical property of a corresponding particle $p_i$ in $\{p_1, \ldots, p_N\}$. Examples of such physical properties include, but are not limited to, an accessible surface area or solvent-excluded surface area of a plurality of atoms in the complex molecule represented by the corresponding particle $p_i$. Further examples of such physical properties include, but are not limited to, an electrical charge, hydrophobicity, hydrophilicity, polarity, aromaticity, molecular weight, or volume of the plurality of atoms in the complex molecule that are represented by the corresponding particle $p_i$.

In some embodiments, the programs or modules identified above correspond to sets of instructions for performing a function described above. The sets of instructions can be executed by one or more processors (e.g., the CPUs 22). The above identified modules or programs (e.g., sets of instructions) need not be implemented as separate software programs, procedures or modules, and thus various subsets of these programs or modules may be combined or otherwise re-arranged in various embodiments. In some embodiments, memory 36 stores a subset of the modules and data structures identified above. Furthermore, memory 36 may store additional modules and data structures not described above.

Figure 2:
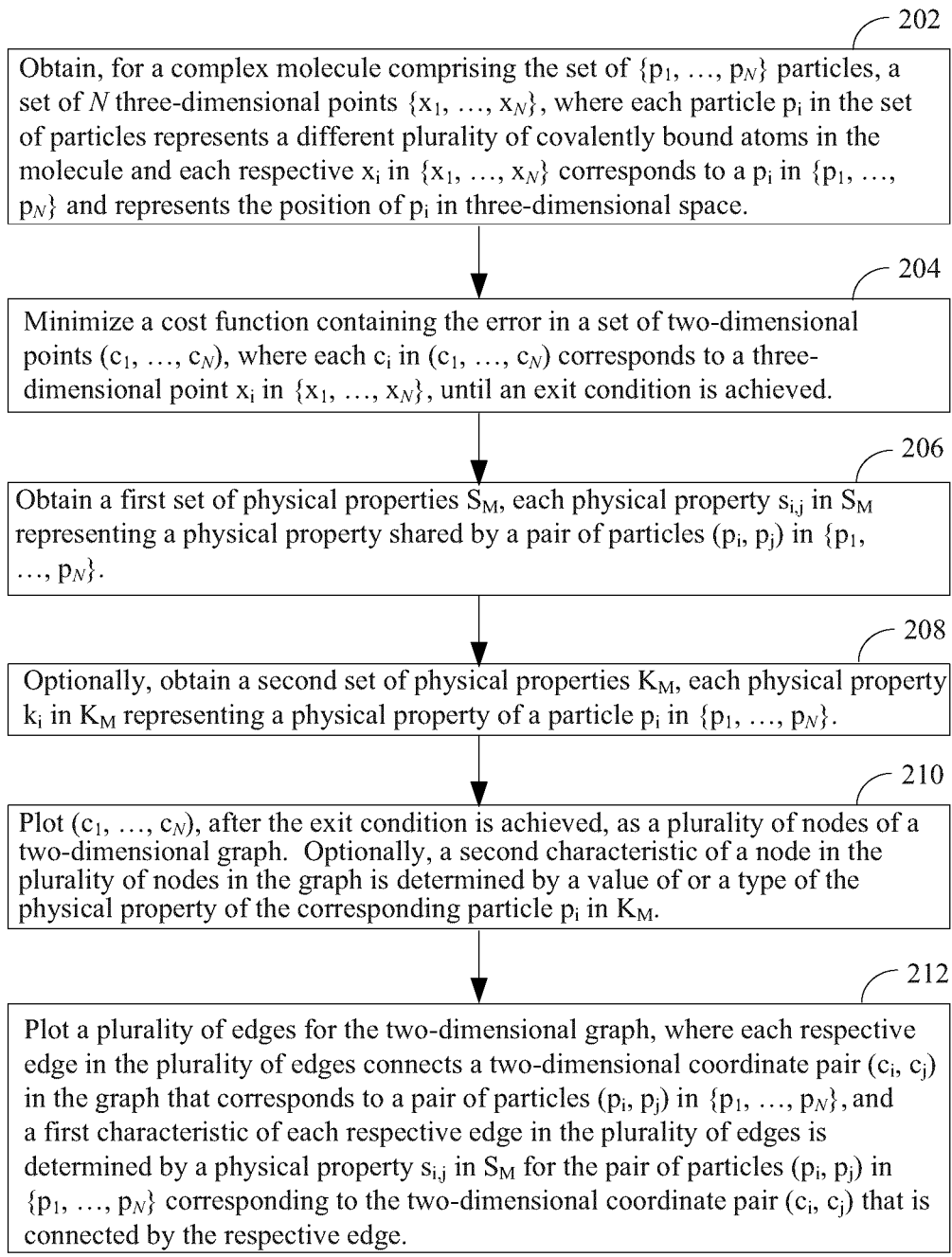
FIG. 2 illustrates a method for visualizing complex molecules in two dimensions, according to some embodiments.

Now that a system in accordance with the systems and methods of the present disclosure has been described, attention turns to FIG. 2 which illustrates an exemplary method in accordance with the present disclosure.

Step 202.

In step 202, a set of N three-dimensional coordinates $\{x_1, \ldots, x_N\}$ 48 is obtained for a complex molecule comprising a set of $\{p_1, \ldots, p_N\}$ particles 46. Each particle $p_i$ in the set of $\{p_1, \ldots, p_N\}$ particles represents a different plurality of covalently bound atoms in the complex molecule. In one example, the complex molecule is a polynucleic acid and each particle $p_i$ in the set of $\{p_1, \ldots, p_N\}$ particles represents a nucleic acid residue in the polynucleic acid. In another example, the complex molecule is a polyribonucleic acid and each particle $p_i$ in the set of $\{p_1, \ldots, p_N\}$ particles represents a ribonucleic acid residue in the polyribonucleic acid. In still another example, the complex molecule is a polysaccharide and each particle $p_i$ in the set of $\{p_1, \ldots, p_N\}$ particles represents a monosaccharide unit or a disaccharide unit in the polysaccharide.

In still another example, the macromolecule is a protein and each particle $p_i$ in the set of $\{p_1, \ldots, p_N\}$ particles represents a residue in the protein. In some such embodiments, each respective $x_i$ in $\{x_1, \ldots, x_N\}$ is the three-dimensional coordinates of the $C_\alpha$ carbon of the residue represented by the $p_i$ in the set of $\{p_1, \ldots, p_N\}$ particles that corresponds to the respective $x_i$.

In still another example, the macromolecule is a protein or polypeptide and each particle $p_i$ in the set of $\{p_1, \ldots, p_N\}$ particles represents a residue in the protein polypeptide. In some such embodiments, each respective $x_i$ in $\{x_1, \ldots, x_N\}$ is the three-dimensional coordinate of the center of mass of the residue represented by the $p_i$ in the set of $\{p_1, \ldots, p_N\}$ particles that corresponds to the respective $x_i$.

In still another example, the complex molecule is a polymer and each particle $p_i$ in the set of $\{p_1, \ldots, p_N\}$ particles represents one or more different residues in the polymer. A polymer is a large molecule composed of repeating structural units. These repeating structural units are termed particles herein. In some embodiments, each particle $p_i$ in the set of $\{p_1, \ldots, p_N\}$ particles represents a single different residue in the polymer. To illustrate, consider the case where the polymer comprises 100 residues. In this instance, the set of $\{p_1, \ldots, p_N\}$ comprises 100 particles, with each particle in $\{p_1, \ldots, p_N\}$ representing a different one of the 100 particles. In another example, in some embodiments, each particle $p_i$ in the set of $\{p_1, \ldots, p_N\}$ particles represents a pair of particles in the polymer. In this instance, the set of $\{p_1, \ldots, p_N\}$ comprises 50 particles, with each particle in $\{p_1, \ldots, p_N\}$ representing a different one of the 50 particles. In some embodiments, the polymer is a natural material. In some embodiments, the polymer is a synthetic material. In some embodiments, the polymer is an elastomer, shellac, amber, natural or synthetic rubber, cellulose, Bakelite, nylon, polystyrene, polyethylene, polypropylene, or polyacrylonitrile, polyethylene glycol, or polysaccharide.

In some embodiments, the complex molecule is a heteropolymer (copolymer). A copolymer is a polymer derived from two (or more) monomeric species, as opposed to a homopolymer where only one monomer is used. Copolymerization refers to methods used to chemically synthesize a copolymer. Examples of copolymers include, but are not limited to, ABS plastic, SBR, nitrile rubber, styrene-acrylonitrile, styrene-isoprene-styrene (SIS) and ethylene-vinyl acetate. Since a copolymer consists of at least two types of constituent units (also structural units, or particles), copolymers can be classified based on how these units are arranged along the chain. These include alternating copolymers with regular alternating A and B units. See, for example, Jenkins, 1996, "Glossary of Basic Terms in Polymer Science," Pure Appl. Chem. 68 (12): 2287-2311, which is hereby incorporated herein by reference in its entirety. Additional examples of copolymers are periodic copolymers with A and B units arranged in a repeating sequence (e.g. $(A-B-A-B-B-A-A-A-A-B-B-B)_n$). Additional examples of copolymers are statistical copolymers in which the sequence of monomer residues in the copolymer follows a statistical rule. If the probability of finding a given type monomer residue at a particular point in the chain is equal to the mole fraction of that monomer residue in the chain, then the polymer may be referred to as a truly random copolymer. See, for example, Painter, 1997, *Fundamentals of Polymer Science*, CRC Press, 1997, p 14, which is hereby incorporated by reference herein in its entirety. Still other examples of copolymers are block copolymers comprising two or more homopolymer subunits linked by covalent bonds. The union of the homopolymer subunits may require an intermediate non-repeating subunit, known as a junction block. Block copolymers with two or three distinct blocks are called diblock copolymers and triblock copolymers, respectively.

In some embodiments, the complex molecule of interest is in fact a plurality of polymers, where the polymers in the plurality of polymers do not all have the same molecular weight. In such embodiments, the polymers in the plurality of polymers fall into a weight range with a corresponding distribution of chain lengths. In some embodiments, the polymer is a branched polymer molecule comprising a main chain with one or more substituent side chains or branches. Types of branched polymers include, but are not limited to, star polymers, comb polymers, brush polymers, dendronized polymers, ladders, and dendrimers. See, for example, Rubinstein et al., 2003, *Polymer physics*, Oxford; N.Y.: Oxford University Press. p. 6, which is hereby incorporated by reference herein in its entirety.

In some embodiments, the complex molecule of interest is a polypeptide. As used herein, the term "polypeptide" means two or more amino acids or residues linked by a peptide bond. The terms "polypeptide" and "protein" are used interchangeably and include oligopeptides and peptides. An "amino acid," "residue" or "peptide" refers to any of the twenty standard structural units of proteins as known in the art, which include imino acids, such as proline and hydroxyproline. The designation of an amino acid isomer may include D, L, R and S. The definition of amino acid includes nonnatural amino acids. Thus, selenocysteine, pyrrolysine, lanthionine, 2-aminoisobutyric acid, gamma-aminobutyric acid, dehydroalanine, ornithine, citrulline and homocysteine are all considered amino acids. Other variants or analogs of the amino acids are known in the art. Thus, a polypeptide may include synthetic peptidomimetic structures such as peptoids. See Simon et al., 1992, Proceedings of the National Academy of Sciences USA, 89, 9367, which is hereby incorporated by reference herein in its entirety. See also Chin et al., 2003, Science 301, 964; and Chin et al., 2003, Chemistry & Biology 10, 511, each of which is incorporated by reference herein in its entirety.

A polypeptide may also have any number of posttranslational modifications. Thus, a polypeptide includes those that are modified by acylation, alkylation, amidation, biotinylation, formylation, γ-carboxylation, glutamylation, glycosylation, glycylation, hydroxylation, iodination, isoprenylation, lipoylation, cofactor addition (for example, of a heme, flavin, metal, etc.), addition of nucleosides and their derivatives, oxidation, reduction, pegylation, phosphatidylinositol addition, phosphopantetheinylation, phosphorylation, pyroglutamate formation, racemization, addition of amino acids by tRNA (for example, arginylation), sulfation, selenoylation, ISGylation, SUMOylation, ubiquitination, chemical modifications (for example, citrullination and deamidation), and treatment with other enzymes (for example, proteases, phosphotases and kinases). Other types of posttranslational modifications are known in the art and are also included.

In some embodiments, the complex molecule of interest is an organometallic complex. An organometallic complex is chemical compound containing bonds between carbon and metal. In some instances, organometallic compounds are distinguished by the prefix "organo-" e.g. organopalladium compounds. Examples of such organometallic compounds include all Gilman reagents, which contain lithium and copper. Tetracarbonyl nickel, and ferrocene are examples of organometallic compounds containing transition metals. Other examples include organomagnesium compounds like iodo(methyl)magnesium MeMgI, diethylmagnesium ($Et_2Mg$), and all Grignard reagents; organolithium compounds such as n-butyllithium (n-BuLi), organozinc compounds such as diethylzinc ($Et_2Zn$) and chloro(ethoxycarbonylmethyl)zinc ($ClZ_nCH_2C(=O)OEt$); and organocopper compounds such as lithium dimethylcuprate ($Li^+[CuMe_2]^-$). In addition to the traditional metals, lanthanides, actinides, and semimetals, elements such as boron, silicon, arsenic, and selenium are considered form organometallic compounds, e.g. organoborane compounds such as triethylborane ($Et_3B$).

In some embodiments, the complex molecule of interest is a surfactant. Surfactants are compounds that lower the surface tension of a liquid, the interfacial tension between two liquids, or that between a liquid and a solid. Surfactants may act as detergents, wetting agents, emulsifiers, foaming agents, and dispersants. Surfactants are usually organic compounds that are amphiphilic, meaning they contain both hydrophobic groups (their tails) and hydrophilic groups (their heads). Therefore, a surfactant molecule contains both a water insoluble (or oil soluble) component and a water soluble component. Surfactant molecules will diffuse in water and adsorb at interfaces between air and water or at the interface between oil and water, in the case where water is mixed with oil. The insoluble hydrophobic group may extend out of the bulk water phase, into the air or into the oil phase, while the water soluble head group remains in the water phase. This alignment of surfactant molecules at the surface modifies the surface properties of water at the water/air or water/oil interface.

Examples of ionic surfactants include ionic surfactants such as anionic, cationic, or zwitterionic (ampoteric) surfactants. Anionic surfactants include (i) sulfates such as alkyl sulfates (e.g., ammonium lauryl sulfate, sodium lauryl sulfate), alkyl ether sulfates (e.g., sodium laureth sulfate, sodium myreth sulfate), (ii) sulfonates such as docusates (e.g., dioctyl sodium sulfosuccinate), sulfonate fluorosurfactants (e.g., perfluorooctanesulfonate and perfluorobutanesulfonate), and alkyl benzene sulfonates, (iii) phosphates such as alkyl aryl ether phosphate and alkyl ether phosphate, and (iv) carboxylates such as alkyl carboxylates (e.g., fatty acid salts (soaps) and sodium stearate), sodium lauroyl sarcosinate, and carboxylate fluorosurfactants (e.g., perfluorononanoate, perfluorooctanoate, etc.). Cationic surfactants include pH-dependent primary, secondary, or tertiary amines and permanently charged quaternary ammonium cations. Examples of quaternary ammonium cations include alkyltrimethylammonium salts (e.g., cetyl trimethylammonium bromide, cetyl trimethylammonium chloride), cetylpyridinium chloride (CPC), benzalkonium chloride (BAC), benzethonium chloride (BZT), 5-bromo-5-nitro-1,3-dioxane, dimethyldioctadecylammonium chloride, and dioctadecyldimethylammonium bromide (DODAB). Zwitterionic surfactants include sulfonates such as CHAPS (3-[(3-Cholamidopropyl)dimethylammonio]-1-propanesulfonate) and sultaines such as cocamidopropyl hydroxysultaine. Zwitterionic surfactants also include carboxylates and phosphates.

Nonionic surfactants include fatty alcohols such as cetyl alcohol, stearyl alcohol, cetostearyl alcohol, and oleyl alcohol. Nonionic surfactants also include polyoxyethylene glycol alkyl ethers (e.g., octaethylene glycol monododecyl ether, pentaethylene glycol monododecyl ether), polyoxypropylene glycol alkyl ethers, glucoside alkyl ethers (decyl glucoside, lauryl glucoside, octyl glucoside, etc.), polyoxyethylene glycol octylphenol ethers ($C_8H_{17}$—($C_6H_4$)—(O—$C_2H_4$)$_{1-25}$—OH), polyoxyethylene glycol alkylphenol ethers ($C_9H_{19}$—($C_6H_4$)—(O—$C_2H_4$)$_{1-25}$—OH, glycerol alkyl esters (e.g., glyceryl laurate), polyoxyethylene glycol sorbitan alkyl esters, sorbitan alkyl esters, cocamide MEA, cocamide DEA, dodecyldimethylamine oxideblock copolymers of polyethylene glycol and polypropylene glycol (poloxamers), and polyethoxylated tallow amine. In some embodiments, the complex molecule is a reverse micelle, or liposome.

In some embodiments, the complex molecule is a fullerene. A fullerene is any molecule composed entirely of carbon, in the form of a hollow sphere, ellipsoid or tube. Spherical fullerenes are also called buckyballs, and they resemble the balls used in association football. Cylindrical ones are called carbon nanotubes or buckytubes. Fullerenes are similar in structure to graphite, which is composed of stacked graphene sheets of linked hexagonal rings; but they may also contain pentagonal (or sometimes heptagonal) rings.

In some embodiments, the set of N three-dimensional coordinates $\{x_1, \ldots, x_N\}$ 48 for the complex molecule of interest are obtained by x-ray crystallography, nuclear magnetic resonance spectroscopic techniques, or electron microscopy. In some embodiments, the set of N three-dimensional coordinates $\{x_1, \ldots, x_N\}$ is obtained by modeling (e.g., molecular dynamics simulations).

In some embodiments, the complex molecule is a macromolecule and each particle $p_i$ in the set of $\{p_1, \ldots, p_N\}$ particles represents more than one residue of the macromolecule. For instance, in some embodiments, each particle represents two residues of the macromolecule. In some embodiments, each particle represents three residues of the macromolecule. In some embodiments, each particle represents four residues of the macromolecule. In some embodiments, the macromolecule includes two different types of polymers, such as a nucleic acid bound to a polypeptide. In some embodiments, the macromolecule includes two polypeptides bound to each other. In some embodiments, the macromolecule includes one or more metal ions (e.g. a metalloproteinase with one or more zinc atoms) and/or is bound to one or more organic small molecules (e.g., an inhibitor). In such instances, the metal ions and or the organic small molecules may be represented as one or more additional particles $p_i$ in the set of $\{p_1, \ldots, p_N\}$ particles representing the macromolecule.

In some embodiments, there are ten or more, twenty or more, thirty or more, fifty or more, one hundred or more, between one hundred and one thousand, or less than 500 particles in the complex molecule.

There is no requirement that each atom in a particle $p_i$ be covalently bound to each other atom in the particle. More typically, each atom in a particle $p_i$ is covalently bound to at least one other atom in the particle, as is the typical case in an amino acid residue in a polypeptide. Moreover, typically, for each respective particle $p_i$ in the set of $\{p_1, \ldots, p_N\}$ particles, there is at least one atom in the respective particle $p_i$ that is covalently bound to an atom in another particle in the set of $\{p_1, \ldots, p_N\}$ particles.

Step 204.

In step 204, a cost function containing the error in a set of two-dimensional coordinates $(c_1, \ldots, c_N)$, where each $c_i$ in $(c_1, \ldots, c_N)$ corresponds to a three-dimensional coordinate $x_i$ in $\{x_1, \ldots, x_N\}$, is defined. Once the cost-function has been defined, the next step is to minimize it with respect to the two-dimensional coordinates $(c_1, \ldots, c_N)$. To perform such minimization, an initial configuration for the two-dimensional coordinates $(c_1, \ldots, c_N)$ is obtained. In some embodiments, an initial configuration for the two-dimensional coordinates $(c_1, \ldots, c_N)$ is obtained by applying a linear principal component analysis to the three-dimensional coordinates $\{x_1, \ldots, x_N\}$. In general, an initial configuration for the two-dimensional coordinates $(c_1, \ldots, c_N)$ can be obtained by applying any form of dimension reduction algorithm to the three-dimensional coordinates $\{x_1, \ldots, x_N\}$.

In some embodiments, the cost function has the form:

$$E(c_1, c_2, \ldots, c_N) = \sum_{i<j}^{N} w_{ij} |\delta_{ij} - D(c_i, c_j)|^2$$

where, i and j are integers greater than zero, $\delta_{i,j}$ is a distance between a pair of three-dimensional coordinates $x_i$ and $x_j$ in $\{x_1, \ldots, x_N\}$, $E(c_1, c_2, \ldots, c_N)$ is an error in the set of two-dimensional coordinates $(c_1, \ldots, c_N)$, where each two-dimensional coordinate $c_i$ in $(c_1, \ldots, c_N)$ uniquely corresponds to a three-dimensional coordinate $x_i$ in $\{x_1, \ldots, x_N\}$ so that each respective $p_i$ in $\{p_1, \ldots, p_N\}$ is represented by a three-dimensional coordinate $x_i$ in $\{x_1, \ldots, x_N\}$ and a corresponding two-dimensional coordinate $c_i$ in $(c_1, \ldots, c_N)$, $D(c_i, c_j)$ is a distance between the two-dimensional coordinates $c_i$ and $c_j$ in $(c_1, \ldots, c_N)$, and $w_{ij}$ is a weight for the two-dimensional pair $(p_i, p_j)$ in a matrix of weights, where the matrix of weights has a weight for each two-dimensional pair $(p_i, p_j)$ in $(p_1, \ldots, p_N)$.

In an embodiment in which Sammon mapping is used, the weights are defined as:

$$w_{ij} = \frac{1}{\delta_{ij}} \frac{1}{\sum_{k<l}^{N} \delta_{kl}}$$

where $\delta_{kl}$ is a distance between a pair of three-dimensional coordinates $x_k$ and $x_l$ in $\{x_1, \ldots, x_N\}$. While not intending to be limited by any particular theory, a justification for such weighting according to this formulation is that the separation between two particles that are close in the high-dimensional space will be given a greater weight. Hence, according to this proposed justification, local topology is better preserved than distal particle separations, which often is a desired property.

Once the cost function has been defined and an initial configuration for the two-dimensional coordinates $(c_1, \ldots, c_N)$ determined, any of a range of methods can be used to minimize the cost function until an exit condition is achieved. In some embodiments, the cost function is minimized by steepest decent. When steepest decent minimization is used, derivatives of the cost function are calculated. The derivative of the cost function is derived as follows:

$$\frac{\partial E}{\partial c_m} = \frac{1}{\sum_{k<l}^{N} \delta_{kl}} \sum_{i<j}^{N} \frac{1}{\delta_{ij}} \frac{\partial}{\partial c_m} |\delta_{ij} - D(c_i, c_j)|^2 =$$

$$\frac{1}{\sum_{k<l}^{N} \delta_{kl}} \sum_{j, j \neq m}^{N} \frac{1}{\delta_{mj}} \frac{\partial}{\partial c_m} |\delta_{mj} - D(c_m, c_j)|^2 =$$

$$\frac{-2}{\sum_{k<l}^{N} \delta_{kl}} \sum_{j, j \neq m}^{N} \frac{1}{\delta_{mj}} |\delta_{mj} - D(c_m, c_j)| \frac{\partial}{\partial c_m} D(c_m, c_j) =$$

$$\frac{-2}{\sum_{k<l}^{N} \delta_{kl}} \sum_{j, j \neq m}^{N} \frac{1}{\delta_{mj}} |\delta_{mj} - Dcm, cj(cm - cj)Dcm, cj.$$

where k, N, l, m, i, j are integers greater than zero.

The second equality follows from the observation that derivatives are zero for any distance not involving the particle m. The third equality follows from the chain-rule. The third equality follows from the derivative of the Euclidian distance between particle m and j in a two-dimensional space:

$$D(c_i, c_j) = \sqrt{(c_i^x - c_j^x)^2 + (c_i^y - c_j^y)^2}$$

where the superscript denotes the x- and y-component of the particle coordinate.

In some embodiments, the cost function is minimized using a quasi-Newton method, such as the Broyden-Fletcher-Goldfarb-Shanno (BFGS), which also only requires the above identified derivative. In quasi-Newton methods, the Hessian matrix of second derivatives need not be evaluated directly. Instead, the Hessian matrix is approximated using rank-one updates specified by gradient evaluations (or approximate gradient evaluations). Quasi-Newton methods are a generalization of the secant method to find the root of the first derivative for multidimensional problems. In multi-dimensions the secant equation does not specify a unique solution, and quasi-Newton methods differ in how they constrain the solution.

In some embodiments, the cost function is minimized using a random walk method, such as simulated annealing ("SA"), that does not require derivatives. For applications involving on the order of a few hundred particles a "hill-climbing method", such as steepest decent or BFGS, is expected to be optimal. The SA method is computationally more expensive. For a very large number of particles simulated annealing may be a better minimization technique than the hill-climbing methods.

As noted above, the cost function is minimized until an exit condition is achieved. In some instances, the exit condition is determined by the method by which the cost function is minimized. For example, Berinde, 1997, Novi SAD J. Math, 27, 19-26, which is incorporated herein by reference, outlines some exit conditions for Newton's method. In some embodiments, the exit condition is achieved when a predetermined maximum number of iterations of the refinement algorithm have been computed. In some embodiments, the predetermined maximum number of iterations is ten iterations, twenty iterations, one hundred iterations or one thousand iterations. For a given iteration n, where n is other than the first iteration the starting two-dimensional coordinates $(c_i, \ldots, c_N)$ are the two-dimensional coordinates $(c_1, \ldots, c_N)$ from the $n-1^{th}$ iteration. As discussed above, for the initial run of the refinement method on the initial two-dimensional coordinates $(c_1, \ldots, c_N)$, the two-dimensional coordinates $(c_1, \ldots, c_N)$ that were derived directly from the three dimensional coordinates $\{x_1, \ldots, x_N\}$ is used.

Step 206.

Minimization of the cost function results in a refined set of two-dimensional coordinates $(c_1, \ldots, c_N)$ that represent the three dimensional coordinates of the complex molecule. Steps 206 through 212 of the method are advantageously directed to using this refined set of two-dimensional coordinates $(c_1, \ldots, c_N)$ to visualize physical properties of the complex molecule.

In step 206, a first set of physical properties $S_M$ is obtained. Each physical property $s_{i,j}$ in $S_M$ represents a physical property shared by a pair of particles $(p_i, p_j)$ in $\{p_1, \ldots, p_N\}$.

In some embodiments, the physical property represented by $s_{i,j}$ for the corresponding pair of particles $(p_i, p_j)$ in $\{p_1, \ldots, p_N\}$ is a presence of a covalent bond between a first atom in the plurality of atoms represented by particle $p_i$ and a second atom in the plurality of atoms represented by particle $p_j$, where i does not equal j. An example of such a covalent bond arises in the case where the pair of particles $(p_i, p_j)$ represent a first cysteine $(p_i)$ and a second cysteine $(p_j)$ and the two cysteines form a disulphide bond.

In some embodiments, the physical property represented by $s_{i,j}$ for the corresponding pair of particles $(p_i, p_j)$ in $\{p_1, \ldots, p_N\}$ is a presence of a hydrogen bond between a first atom in the plurality of atoms represented by particle $p_i$ and a second atom in the plurality of atoms represented by particle $p_j$. Hydrogen bonds are formed when an electronegative atom approaches a hydrogen atom bound to another electronegative atom. The most common electro negative atoms in biochemical systems are oxygen (3.44) and nitrogen (3.04) while carbon (2.55) and hydrogen (2.22) are relatively electropositive. The hydrogen is normally covalently attached to one atom, the donor, but interacts electrostatically with the other, the acceptor. This interaction is due to the dipole between the electronegative atoms and the proton. Thus, the first atom in the plurality of atoms represented by particle $p_i$ is the donor and the second atom in the plurality of atoms represented by particle $p_j$ is the acceptor of the hydrogen, or vice versa. Moreover, the first atom in the plurality of atoms represented by particle $p_i$ and the second atom in the plurality of atoms represented by particle $p_j$ share the same hydrogen. The occurrence of hydrogen bonds in protein structures has been extensively reviewed by Baker & Hubbard, 1984, Prog. Biophy. Mol. Biol., 44, 97-179, which is hereby incorporated by reference herein in its entirety.

In some embodiments, the physical property represented by $s_{i,j}$ for the corresponding pair of particles $(p_i, p_j)$ in $\{p_1, \ldots, p_N\}$ is a presence of a carbon-carbon contact, a carbon-sulfur contact, or a sulfur-sulfur contact between a first atom in the plurality of atoms represented by particle $p_i$ and a second atom in the plurality of atoms represented by particle $p_j$. In some embodiments, a carbon-carbon contact, a carbon-sulfur contact, or a sulfur-sulfur contact occurs when the first atom and the second atom are each independently carbon or sulfur and the first atom and the second atom are within a predetermined distance of each other in the complex molecule. In some embodiments, this predetermined distance is 4.5 Angstroms. In some embodiments, this predetermined distance is 4.0 Angstroms.

In some embodiments, the physical property represented by $s_{i,j}$ for the corresponding pair of particles $(p_i, p_j)$ in $\{p_1, \ldots, p_N\}$ is a presence of a carbon-nitrogen contact between a first atom in the plurality of atoms represented by particle $p_i$ and a second atom in the plurality of atoms represented by particle $p_j$. In some embodiments, a carbon-nitrogen contact occurs when the first atom is a carbon and the second atom is a nitrogen and the first atom and the second atom are within a predetermined distance of each other in the complex molecule as defined by the three-dimensional coordinates $\{x_1, \ldots, x_N\}$. In some embodiments, this predetermined distance is 4.5 Angstroms. In some embodiments, this predetermined distance is 4.0 Angstroms. In some embodiments, this predetermined distance is 3.5 Angstroms.

In some embodiments, the physical property represented by $s_{i,j}$ for the corresponding pair of particles $(p_i, p_j)$ in $\{p_1, \ldots, p_N\}$ is a presence of a carbon-oxygen contact between a first atom in the plurality of atoms represented by particle $p_i$ and a second atom in the plurality of atoms represented by particle $p_j$. In some embodiments, a carbon-oxygen contact occurs when the first atom is a carbon and the second atom is a oxygen and the first atom and the second atom are within a predetermined distance of each other in the complex molecule. In some embodiments, this predetermined distance is 4.5 Angstroms. In some embodiments, this predetermined distance is 4.0 Angstroms. In some embodiments, this predetermined distance is 3.5 Angstroms.

In some embodiments, the physical property represented by $s_{i,j}$ for the corresponding pair of particles $(p_i, p_j)$ in $\{p_1, \ldots, p_N\}$ is a $\pi$-$\pi$ interaction or a $\pi$-cation interaction between a first portion of the plurality of atoms represented by particle $p_i$ and a second portion of the plurality of atoms represented by particle $p_j$. A $\pi$-$\pi$ interaction is an attractive, noncovalent interaction between aromatic rings in which the aromatic rings are parallel to each other or form a T-shaped configuration and their respective centers of mass are approximately five Angstroms apart. See, for example, Brocchieri and Karlin, 1994, PNAS 91:20, 9297-9301, which is hereby incorporated by reference. A $\pi$-cation interaction is a noncovalent molecular interaction between the face of an electron-rich it system (e.g. benzene, ethylene) and an adjacent cation (e.g. $NH_3$ group of lysine, the guanidine group of arginine, etc.). This interaction is an example of noncovalent bonding between a quadrupole ($\pi$ system) and a monopole (cation).

Step 208.

Optionally, in some embodiments, a second set of physical properties $K_M$ is obtained. Whereas the physical properties $S_M$ are for pairs of particles (pi, pj) in $\{p_1, \ldots, p_N\}$, each physical property $k_i$ in $K_M$ represents a physical property of a single particle $p_i$ in $\{p_1, \ldots, p_N\}$. Two examples of physical properties for $K_M$ are accessible surface area and solvent-excluded surface of the plurality of atoms in the complex molecule that are represented by the corresponding particle $p_i$.

The accessible surface area (ASA), also known as the "accessible surface", is the surface area of a biomolecule that is accessible to a solvent. Measurement of ASA is usually described in units of square Angstroms. ASA is described in Lee & Richards, 1971, J. Mol. Biol. 55(3), 379-400, which is hereby incorporated by reference herein in its entirety. ASA can be calculated, for example, using the "rolling ball" algorithm developed by Shrake & Rupley, 1973, J. Mol. Biol. 79(2): 351-371, which is hereby incorporated by reference herein in its entirety. This algorithm uses a sphere (of solvent) of a particular radius to "probe" the surface of the molecule.

The solvent-excluded surface, also known as the molecular surface or Connolly surface, can be viewed as a cavity in bulk solvent (effectively the inverse of the solvent-accessible surface). It can be calculated in practice via a rolling-ball algorithm developed by Richards, 1977, Annu Rev Biophys Bioeng 6, 151-176 and implemented three-dimensionally by Connolly, 1992, J Mol Graphics 11(2), 139-141, each of which is hereby incorporated by reference herein in its entirety.

Additional examples of physical properties for $K_M$ include, but are not limited to, electrical charge, hydrophobicity, hydrophilicity, polarity, aromaticity, molecular weight and volume of the plurality of atoms in the complex molecule that are represented by the corresponding particle $p_i$.

Step 210.

In step 210, the refined two-dimensional coordinates $(c_1, \ldots, c_N)$ are plotted as a plurality of nodes 64 of a two-dimensional graph 62 after the exit condition 58 is achieved. In some embodiments, the refined two-dimensional coordinates $(c_1, \ldots, c_N)$ comprises twenty-five or more nodes and step 210 comprises plotting each of these nodes 64 onto a two-dimensional graph 62. This graph can be stored in memory 36, displayed on display 32, or sent to some other output device such as a printer.

In some embodiments, after the refined two-dimensional coordinates $(c_1, \ldots, c_N)$ are plotted as a plurality of nodes 64 of a two-dimensional graph 62, interaction adjustment module 72 allows for a user to adjust the position of the nodes. In this process, a user adjusts (moves) the coordinates of one or more of the nodes in the plurality of nodes as they are displayed. In some embodiments this is done by a drag and drop operation. Such manual adjustments are then saved to an updated refined set of two-dimensional coordinates $(c_1, \ldots, c_N)$. This useful feature allows for the selective overriding of the cost function minimization for select nodes. The feature provides for the ability to improve the clarity of those instances where the disclosed projection onto a two dimensional plane has produced regions that are not clear. Such regions may arise, for example, when the corresponding local three dimensional structure is intrinsically complicated. In some embodiments, interaction adjustment module 72 allows for a user to delete identified nodes from the two-dimensional graph 62 in order to simplify it.

Optionally, a characteristic 66 of a node 64 in the plurality of nodes in the graph 62 is determined by a value of or a type of the physical property of the corresponding particle $p_i$ in $K_M$ 52. In some embodiments, for each respective node 64 in the plurality of nodes in the graph 62, a characteristic 66 of the respective node 64 is determined by a value of or a type of the physical property of the corresponding particle $p_i$ in $K_M$ 52. In some embodiments, the physical property $k_i$, is an accessible surface area or solvent-excluded surface of the plurality of atoms in the complex molecule that are represented by the corresponding particle $p_i$. In some embodiments, the physical property is an electrical charge, hydrophobicity, hydrophilicity, polarity, aromaticity, molecular weight or volume of the plurality of atoms in the complex molecule that are represented by the corresponding particle $p_i$.

In some embodiments, the characteristic of the node is size and a size of the respective node 64 is determined by a value of or a type of the physical property of the corresponding particle $p_i$ in $K_M$. In some embodiments, the characteristic is shading and a brightness of the shading of the respective node 64 is determined by a value of or the type of the physical property of the corresponding particle $p_i$ in $K_M$. In some embodiments, the characteristic is color and a color of the respective node 64 is determined by a value of or the type of the physical property of the corresponding particle $p_i$ in $K_M$.

In some embodiments, respective characteristics in a plurality of characteristics of the node (e.g., size, shape, shading, color, etc.) each independently represent corresponding physical properties in a plurality of physical properties of the corresponding portion of the complex molecule represented by the corresponding particle $p_i$ in $\{p_1, \ldots, p_N\}$. For example, in some embodiments, one characteristic of the node is size and a size of the respective node 64 is determined by a value of or a type of a first physical property of the corresponding particle $p_i$ in $K_M$ (e.g., polarity), another characteristic is shading and a brightness of the shading of the respective node 64 is determined by a value of or the type of a second physical property of the corresponding particle $p_i$ in $K_M$ (e.g., volume), and a third characteristic is color and a color of the respective node 64 is determined by a value of or the type of a third physical property of the corresponding particle $p_i$ in $K_M$ (e.g., mass).

Step 212.

In step 212, a plurality of edges 68 is plotted for the two-dimensional graph 62. Each respective edge 68 in the plurality of edges connects a two-dimensional coordinate pair $(c_i, c_j)$ (node 64) in the graph 62 that corresponds to a pair of particles $(p_i, p_j)$ in $\{p_1, \ldots, p_N\}$. A characteristic 70 of each respective edge 68 in the plurality of edges 68 is determined by a physical property $s_{i,j}$ in $S_M$ 50 for the pair of particles $(p_i, p_j)$ in $\{p_i, \ldots, p_N\}$ corresponding to the two-dimensional coordinate pair $(c_i, c_j)$ that is connected by the respective edge 68.

In some embodiments, the physical property represented by $s_{i,j}$ for the pair of particles $(p_i, p_j)$ in $\{p_i, \ldots, p_N\}$ is a presence of a covalent bond or hydrogen bond between a first atom in the plurality of atoms represented by particle $p_i$ and a second atom in the plurality of atoms represented by particle $p_j$. In some embodiments, the physical property represented by $s_{i,j}$ for the pair of particles $(p_i, p_j)$ in $\{p_1, \ldots, p_N\}$ is a presence of a carbon-carbon contact, a carbon-sulfur contact, a sulfur-sulfur contact, a carbon-nitrogen contact, or a carbon-oxygen contact between a first atom in the plurality of atoms represented by particle $p_i$ and a second atom in the plurality of atoms represented by particle $p_j$. In some embodiments, the physical property represented by $s_{i,j}$ for the pair of particles $(p_i, p_j)$ in $\{p_1, \ldots, p_N\}$ is a presence of a $\pi$-$\pi$ interaction or a $\pi$-cation interaction between a first atom in the plurality of atoms represented by particle $p_i$ and a second atom in the plurality of atoms represented by particle $p_j$.

In some embodiments, the characteristic is line thickness and a line thickness of an edge in the plurality of edges in the graph is determined by a value of or a type of the physical property in $S_M$ for the pair of particles $(p_i, p_j)$ in $\{p_1, \ldots, p_N\}$ corresponding to the two-dimensional coordinate pair $(c_i, c_j)$ that is connected by the edge. In some embodiments, the characteristic is line coloring and a color of an edge in the plurality of edges in the graph is determined by a value of or a type of the physical property in $S_M$ for the pair of particles $(p_i, p_j)$ in $\{p_1, \ldots, p_N\}$ corresponding to the two-dimensional coordinate pair $(c_i, c_j)$ that is connected by the edge. In some embodiments, the characteristic is line patterning and a pattern of an edge in the plurality of edges in the graph is determined by a value of or a type of the physical property in $S_M$ for the pair of particles $(p_i, p_j)$ in $\{p_1, \ldots, p_N\}$ corresponding to the two-dimensional coordinate pair $(c_i, c_j)$ that is connected by the edge.

In some embodiments, each characteristic in a plurality of characteristics of each respective edge 68 in the plurality of edges 68 is determined by a different physical property $s_{i,j}$ in $S_M$ 50 for the pair of particles $(p_i, p_j)$ in $\{p_1, \ldots, p_N\}$ corresponding to the two-dimensional coordinate pair $(c_i, c_j)$ that is connected by the respective edge 68. For example, in one such embodiment, a first characteristic in the plurality of characteristics for a respective edge 68 is line thickness and a line thickness of the edge 68 is determined by a value of or a type of a first physical property in $S_M$ for the pair of particles $(p_i, p_j)$ in $\{p_1, \ldots, p_N\}$ corresponding to the two-dimensional coordinate pair $(c_i, c_j)$ that is connected by the respective edge 68, a second characteristic in the plurality of characteristics for the respective edge 68 is line coloring and a color of the respective edge is determined by a value of or a type of a second physical property in $S_M$ for the pair of particles $(p_i, p_j)$ in $\{p_1, \ldots, p_N\}$ corresponding to the two-dimensional coordinate pair $(c_i, c_j)$ that is connected by the respective edge 68, and a third characteristic in the plurality of characteristics for the respective edge is line patterning and a pattern of the respective edge 68 is determined by a value of or a type of a third physical property in $S_M$ for the pair of particles $(p_i, p_j)$ in $\{p_1, \ldots, p_N\}$ corresponding to the two-dimensional coordinate pair $(c_i, c_j)$ that is connected by the respective edge 68.

In some embodiments, after the plurality of edges 68 is plotted for the two-dimensional graph 62, interaction adjustment module 72 allows for a user to adjust the position of nodes in the graph. In such embodiments, edges affected by such spatial node adjustments are automatically redrawn so that they continue to connect the same node pairs. In some embodiments, interaction adjustment module 72 allows for a user to adjust edges. In some such embodiments this is done by a drag and drop operation. In some such embodiments, nodes affected by such spatial edge adjustments are automatically repositioned so that they continue to joined by the same edges. Such manual adjustments are then saved to an updated refined set of two-dimensional coordinates $(c_1, \ldots, c_N)$. As in the optional embodiments described above in step 210, this useful feature allows for the selective overriding of the cost function minimization for select nodes in regions that are not clear. In some embodiments, interaction adjustment module 72 allows for a user to delete identified nodes and/or edges from the two-dimensional graph in order to simplify it.

In some embodiments, the two-dimensional graph serves as a graphical table of contents for the information pertaining to individual residues, groups of residues and/or interactions between residues of the complex molecule. In such embodiments, one or more of the nodes 64 and/or edges 68 serve as hyperlinks to free-form text or annotation. Advantageously, this simplifies the browsing and knowledge management of potentially large amount of data and information associated with the complex molecule. Thus, for example, when the two-dimensional graph 62 is shown on display 26, a user clicks on a node 64 or an edge 68 of the graph 62 thereby retrieving hyperlinked information associated with the node or edge. Typically, such hyperlinked information is for the particles $p_i$ in $\{p_1, \ldots, p_N\}$ corresponding to the selected node 64 or edge 68. In some embodiments, the two-dimensional graph is displayed in a web browser and, when the user clicks on a node 64 or an edge 68 of the graph 62, the hyperlinked information associated with the selected node or edge is displayed in a new browser window or in the same browser window displaying the graph 62. Such hyperlinked information can be, for example, any physical properties in $S_M$ or $K_M$, annotation information, inhibitor information (e.g., binding constants, etc.).

Examples

Figure 3:
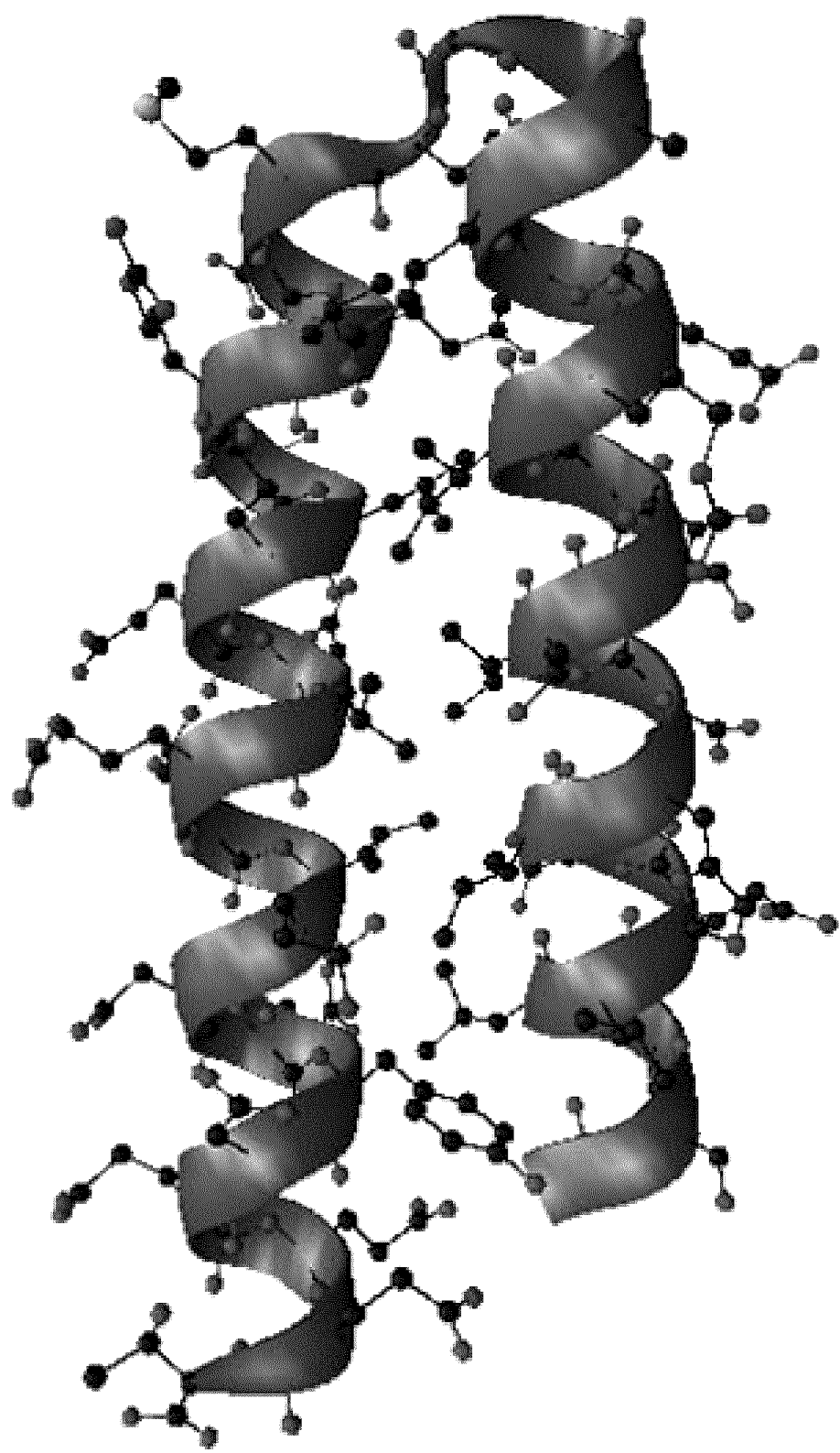
FIG. 3 illustrates a three dimensional representation of the Rab4 binding domain (PDB accession code 1YZM) consisting of two slightly tilted helices in contact, in accordance with the prior art.
Figure 4:
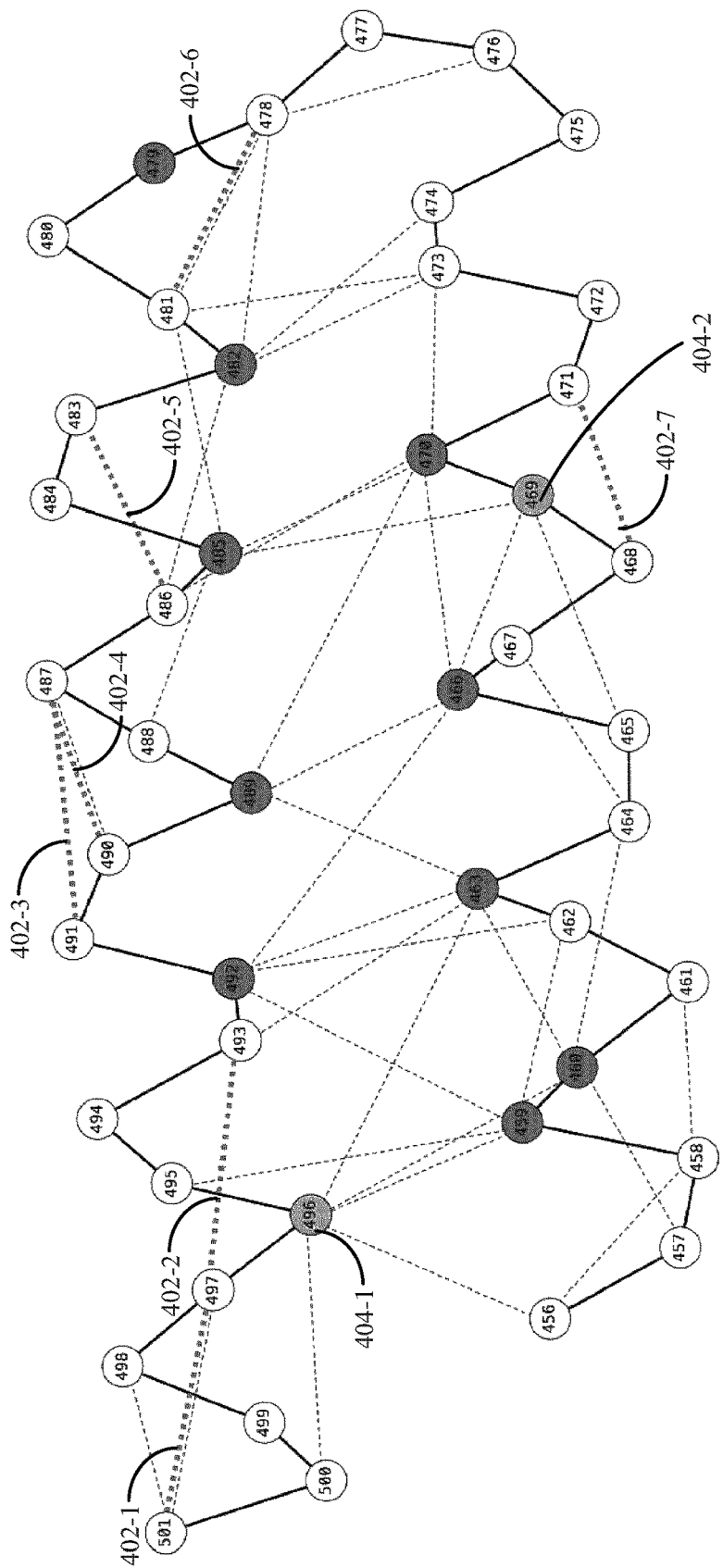
FIG. 4 illustrates the Rab4 binding domain of FIG. 3 rendered as a two dimensional graph with nodes and edges and conveying physical information about residues of the Rab4 binding domain in accordance with the systems and methods of the present disclosure. Solid lines connect residues that share a covalent peptide bond, thick dashed lines represent hydrogen bonds where at least one of the corresponding residue partners include a side-chain atom on the hydrogen bond, dashed lines represent carbon-carbon contacts, dark gray circles represent aliphatic residues, light gray circles represent aromatic residues, and white circles represent polar residues.

Now that exemplary systems and methods in accordance with embodiments of the present disclosure have been presented, illustrations of the results of the systems and methods are provided. FIG. 3 illustrates a three dimensional representation of the Rab4 binding domain (PDB accession code 1YZM) consisting of two slightly tilted helices in contact, in accordance with the prior art. FIG. 4 illustrates the Rab4 binding domain of FIG. 3 rendered as a two dimensional graph with nodes 64 (circles) and edges 68 (lines) and conveying physical information about residues of the Rab4 binding domain in accordance with the systems and methods of the present disclosure. In FIG. 4, solid lines connect residues that share a covalent peptide bond, thick dashed lines 402 represent hydrogen bonds where at least one of the corresponding residue partners include a side-chain atom on the hydrogen bond, dashed lines represent carbon-carbon contacts, dark gray circles represent aliphatic residues, light gray circles 404 represent aromatic residues, and white circles represent polar residues.

Figure 5:
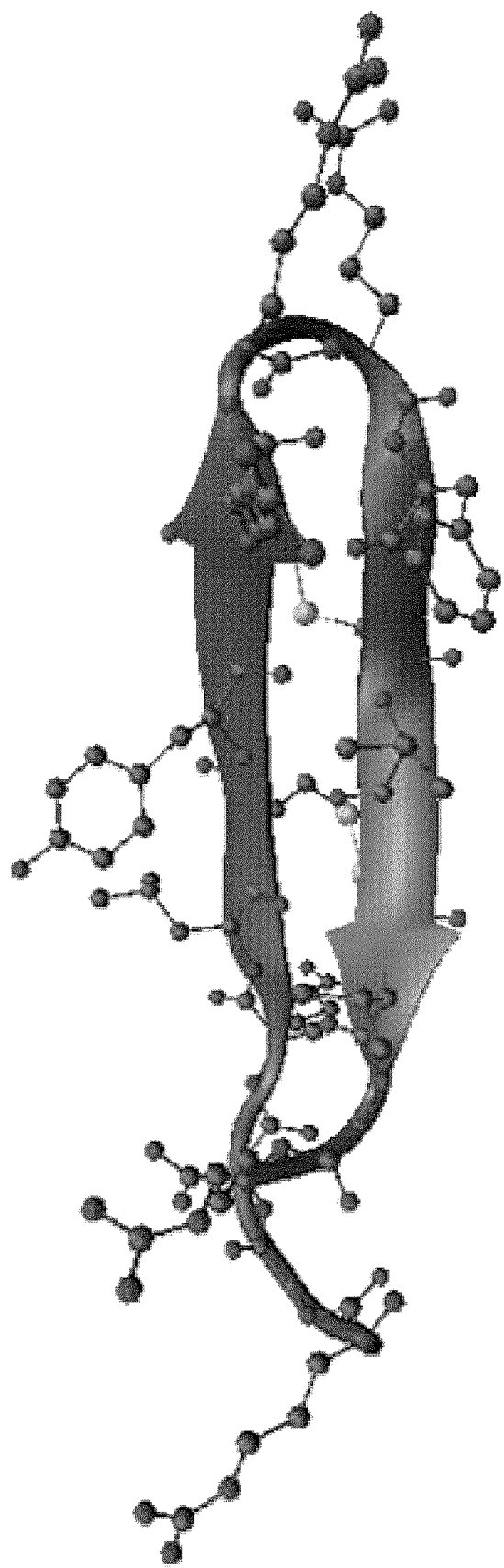
FIG. 5 illustrates a three dimensional representation of the beta strand in accordance with the prior art.
Figure 6:
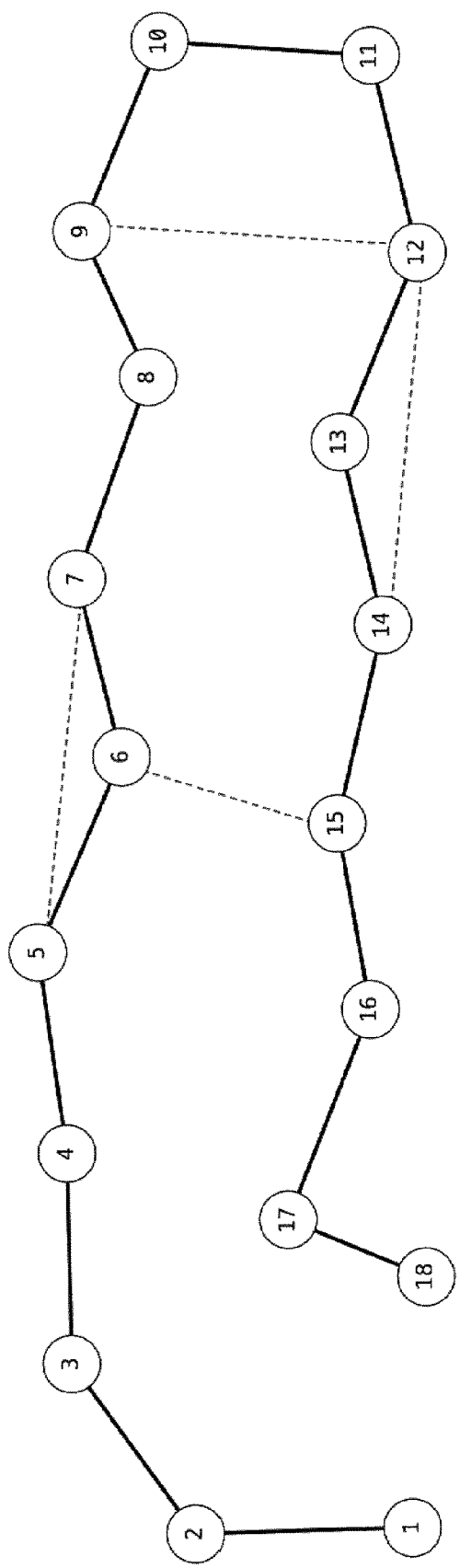
FIG. 6 illustrates the beta strand of FIG. 5 rendered as a two dimensional graph with nodes and edges and conveying physical information about residues of the beta strand of FIG. 5 in accordance with the systems and methods of the present disclosure.

FIG. 5 illustrates a three dimensional representation of the beta strand in accordance with the prior art. FIG. 6 illustrates the beta strand of FIG. 5 rendered as a two dimensional graph with nodes 65 (circles) and edges 68 (lines) conveying physical information about residues of the beta strand of FIG. 5, in accordance with the systems and methods of the present disclosure.

Figure 7:
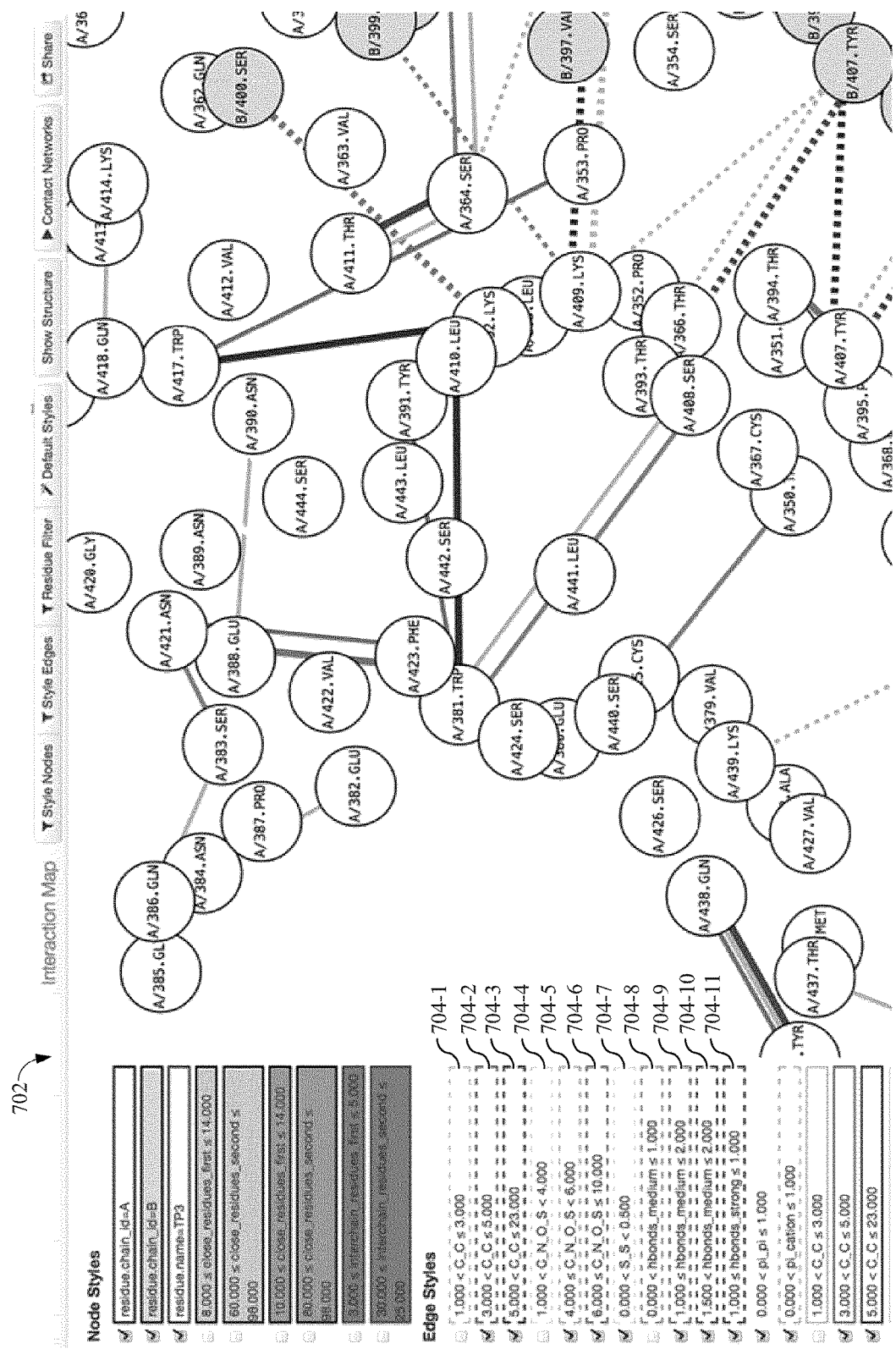
FIG. 7 illustrates a graphical user interface for performing the plotting of two-dimensional coordinates $(c_1, \ldots, c_N)$, after an exit condition is achieved, as a plurality of nodes and for plotting edges for two-dimensional graphs associated with the plurality of nodes in accordance with the systems and methods of the present disclosure.

FIG. 7 illustrates a graphical user interface for performing the plotting of two-dimensional coordinates $(c_1, \ldots, c_N)$, after an exit condition is achieved, as a plurality of nodes and for plotting edges for two-dimensional graphs associated with the plurality of nodes in accordance with the systems and methods of the present disclosure. In particular, as disclosed above, for a molecule that comprises a set of $\{p_1, \ldots, p_N\}$ particles, each particle $p_i$ in the set of particles representing a different plurality of covalently bound atoms in the molecule, there is obtained a set of N three-dimensional coordinates $\{x_1, \ldots, x_N\}$, where each respective $x_i$ in $\{x_1, \ldots, x_N\}$ corresponds to a $p_i$ in $\{p_1, \ldots, p_N\}$ and represents the position of $p_i$ in three-dimensional space. The, a cost function:

$$E(c_1, c_2, \ldots, c_N) = \sum_{i<j}^{N} w_{ij} |\delta_{ij} - D(c_i, c_j)|^2$$

is minimized, where i and j are integers greater than zero, $\delta_{ij}$ is a distance between a pair of three-dimensional coordinates $x_i$ and $x_j$ in $\{x_1, \ldots, x_N\}$, $E(c_1, c_2, \ldots, c_N)$ is an error in the set of two-dimensional coordinates $(c_1, \ldots, c_N)$, and where each two-dimensional coordinate $c_i$ in $(c_1, \ldots, c_N)$ uniquely corresponds to a three-dimensional coordinate $x_i$ in $\{x_1, \ldots, x_N\}$ so that each respective $p_i$ in $\{p_1, \ldots, p_N\}$ is represented by a three-dimensional coordinate $x_i$ in $\{x_1, \ldots, x_N\}$ and a corresponding two-dimensional coordinate $c_i$ in $(c_1, \ldots, c_N)$, $D(c_i, c_j)$ is a distance between the two-dimensional coordinates $c_i$ and $c_j$ in $(c_i, \ldots, c_N)$, and $w_{ij}$ is a weight for the two-dimensional pair $(p_i, p_j)$ in a matrix of weights, where the matrix of weights has a weight for each two-dimensional pair $(p_i, p_j)$ in $(p_1, \ldots, p_N)$, and where the minimizing alters the values of coordinates of the set of two-dimensional coordinates $(c_1, c_N)$ using a refinement algorithm until an exit condition is achieved. Further there is obtained one or more sets of physical properties $S_{Mk}$, each physical property $s_{i,j}$ in $S_{Mk}$ representing a respective physical property k shared by a pair of particles $(p_i, p_j)$ in $\{p_1, \ldots, p_N\}$. In some embodiments, these physical properties are associated with the three dimensional coordinates of the molecule. For instance, one exemplary property is carbon-carbon distance. Another exemplary property is sulfur-sulfur distance. In practice, there can be any number of properties. Moreover, in some embodiments a property is further defined by threshold values. For instance, one property can be 1.0<C–C<3.0, meaning all carbon-carbon interactions in the molecule that are between 1 and 3 Angstroms in length, while another property can be 3.0<C–C<5.0, meaning all carbon-carbon interactions in the molecule that are between 3 and 5 Angstroms in length. As illustrated in FIG. 7, there is provided a graphical user interface 702 that plots $(c_1, \ldots, c_N)$, after the exit condition is achieved, as a plurality of nodes of a two-dimensional graph and plots a first plurality of edges for the two-dimensional graph, where each respective edge in the first plurality of edges connects a two-dimensional coordinate pair $(c_i, c_j)$ in the graph that corresponds to a pair of particles $(p_i, p_j)$ in $\{p_1, \ldots, p_N\}$, and a first characteristic of each respective edge in the first plurality of edges is determined by a respective physical property $s_{i,j}$ in $S_{M1}$ for the pair of particles $(p_i, p_j)$ in $\{p_1, \ldots, p_N\}$ corresponding to the two-dimensional coordinate pair $(c_i, c_j)$ that is connected by the respective edge. In some embodiments the plotting of the edges is done on a conditional basis in which each respective edge is conditionally plotted as a function of a physical property for the pair of particles $(p_i, p_j)$ in $\{p_1, \ldots, p_N\}$ corresponding to the two-dimensional coordinate pair $(c_i, c_j)$ that is connected by the respective edge. Since multiple properties can be defined, this can lead to the plotting of several different edges on a conditional basis as a function of respective physical properties for the pair of particles $(p_i, p_j)$ in $\{p_1, \ldots, p_N\}$ corresponding to the two-dimensional coordinate pair $(c_i, c_j)$ that is connected by the respective edge. In FIG. 7, these edge properties are referred to as edge styles 704.

In some embodiments the plotting of the edges is done on a conditional basis in which each respective edge in the plurality of edges is conditionally plotted as a function of the respective physical property $s_{i,j}$ in $SM_1$ for the pair of particles $(p_i, p_j)$ in $\{p_i, \ldots, p_N\}$ corresponding to the two-dimensional coordinate pair $(c_i, c_j)$ that is connected by the respective edge. For instance, the edges that adhere to the edge style 3.0<C_C≤5.000 704-2 (carbon-carbon interactions greater than 3.0 Angstroms but less than or equal to 5.000 Angstroms) are plotted.

In some embodiments a second plurality of edges for the two-dimensional graph is plotted in which each respective edge in the second plurality of edges connects a two-dimensional coordinate pair $(c_i, c_j)$ in the graph that corresponds to a pair of particles $(p_i, p_j)$ in $\{p_1, \ldots, p_N\}$, and a first characteristic of each respective edge in the second plurality of edges is determined by a respective physical property $s_{i,j}$ in $S_{M2}$ for the pair of particles $(p_i, p_j)$ in $\{p_1, \ldots, p_N\}$ corresponding to the two-dimensional coordinate pair $(c_i, c_j)$ that is connected by the respective edge. For instance, the edges that are adhere to the edge style 5.0<C_C≤23.000 (carbon-carbon interactions greater than 5.0 Angstroms or less than or equal to 23.000 Angstroms) 704-3 are plotted independent of whether or not edges that adhere to the edge style 3.0<C_C≤5.000 704-2 are plotted or not. It will be appreciated in such embodiments that edges may be drawn to the same node using multiple different styles. Moreover, as illustrated in FIG. 7, edge styles are each given a characteristic graphic form (e.g., line thickness, line type, line color, line stipple, etc.) so that it is possible to see the corresponding edges in the graph.

In some embodiments, a third plurality of edges for the two-dimensional graph is plotted in which each respective edge in the third plurality of edges connects a two-dimensional coordinate pair $(c_i, c_j)$ in the graph that corresponds to a pair of particles $(p_i, p_j)$ in $\{p_1, \ldots, p_N\}$ and a first characteristic of each respective edge in the third plurality of edges is determined by a respective physical property $s_{i,j}$ in $S_{M3}$ for the pair of particles $(p_i, p_j)$ in $\{p_1, \ldots, p_N\}$ corresponding to the two-dimensional coordinate pair $(c_i, c_j)$ that is connected by the respective edge. For instance, referring to FIG. 7, the edges that adhere to the edge style 4.000≤C_N_O_S<6.0 704-6 are plotted independent of whether the edges that adhere to the edge style 5.0<C_C≤23.000 704-3 are plotted and independent of whether or not edges that adhere to the edge style 3.0<C_C≤5.000 704-2 are plotted. In practice, as discussed above, there can be any number of edge styles and thus any number of pluralities of edges for the two-dimensional graph.

As illustrated in FIG. 7, a first edge in the first plurality of edges is not plotted when the physical property $s_{i,j}$ does not satisfy a first threshold condition and the first edge is plotted by the plotting (E) when the physical property satisfies the first threshold condition. For example, referring to edge property 3.0<C_C≤5.000 704-2 edges that have a carbon-carbon distance that is greater than 3.0 Angstroms but less than or equal to 5.0 Angstroms are plotted whereas edges between nodes that represent particles that do not have an inter-particle carbon-carbon interaction that is greater than 3.0 Angstroms but less than or equal to 5.0 Angstroms are not plotted.

Figure 8:
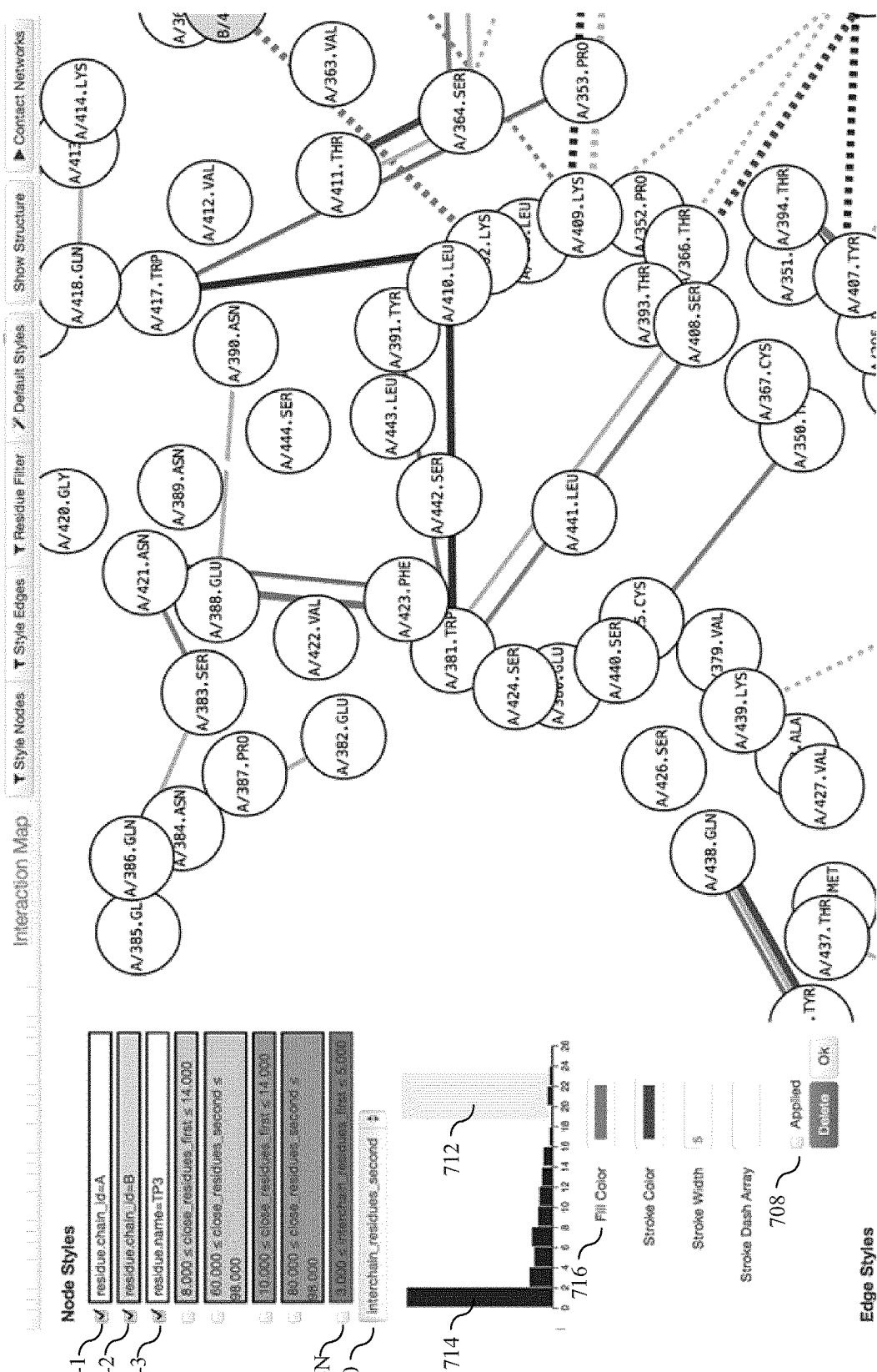
FIG. 8 illustrates the graphical user interface of FIG. 7 in which multiple node styles and edge styles are defined and the respective edges and nodes are toggled on and off based on node style and edge style in accordance with the systems and methods of the present disclosure.

FIG. 8 illustrates the graphical user interface of FIG. 7 in which multiple node styles and edge styles are defined and the respective edges and nodes are toggled on and off based on node style and edge style in accordance with the systems and methods of the present disclosure.

Figure 9:
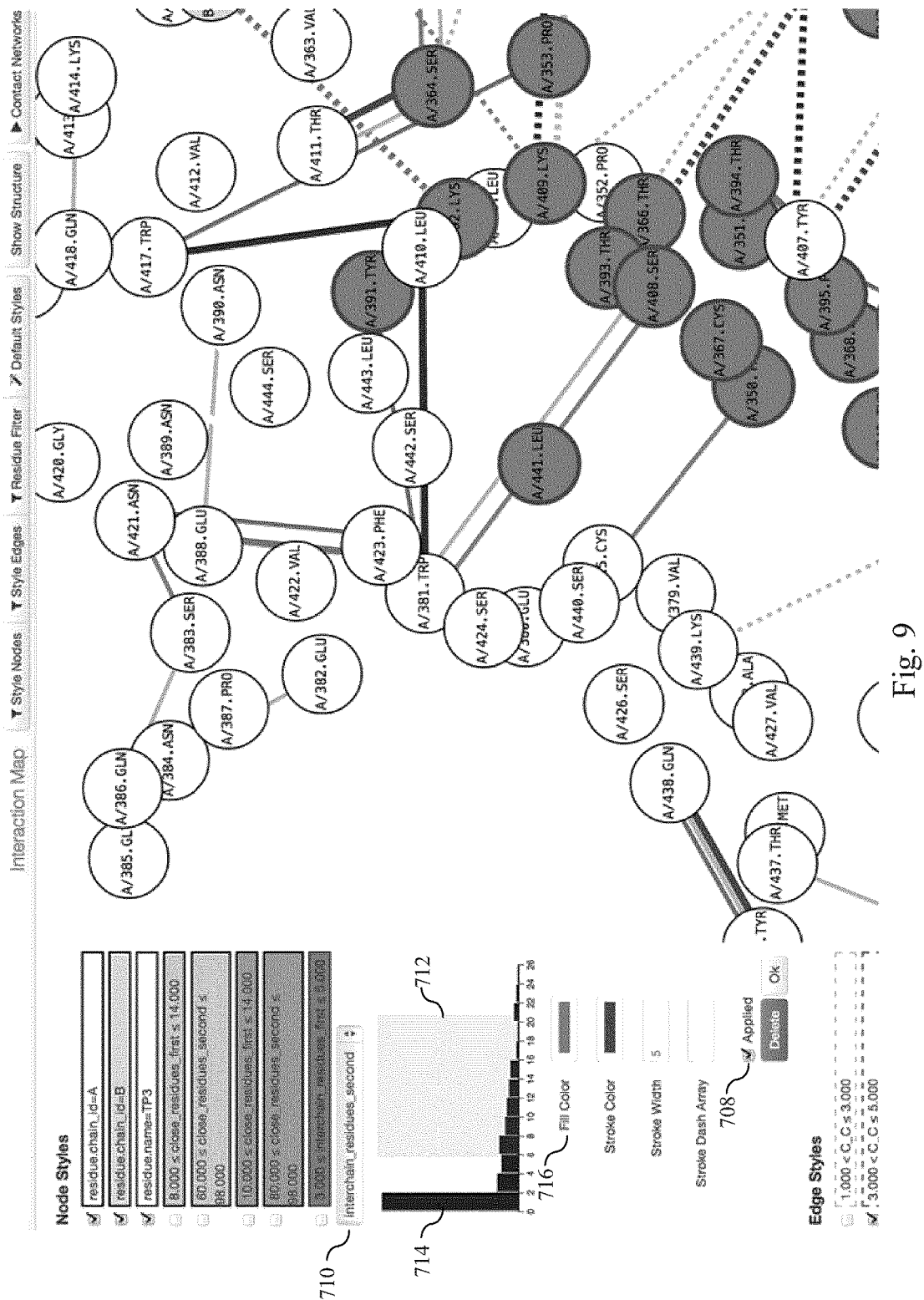
FIGS. 9 and 10 illustrate alternative views of the graphical user interface of FIG. 8 in which in each respective node in the plurality of nodes is associated with one or more properties associated with the respective particle $p_i$ in $\{p_1, \ldots, p_N\}$ represented by the respective node and wherein nodes in the plurality of nodes is conditionally graphically highlighted as a function of the one or more properties associated with the respective particles $p_i$ in $\{p_1, \ldots, p_N\}$ corresponding to the plurality of nodes.
Figure 10:
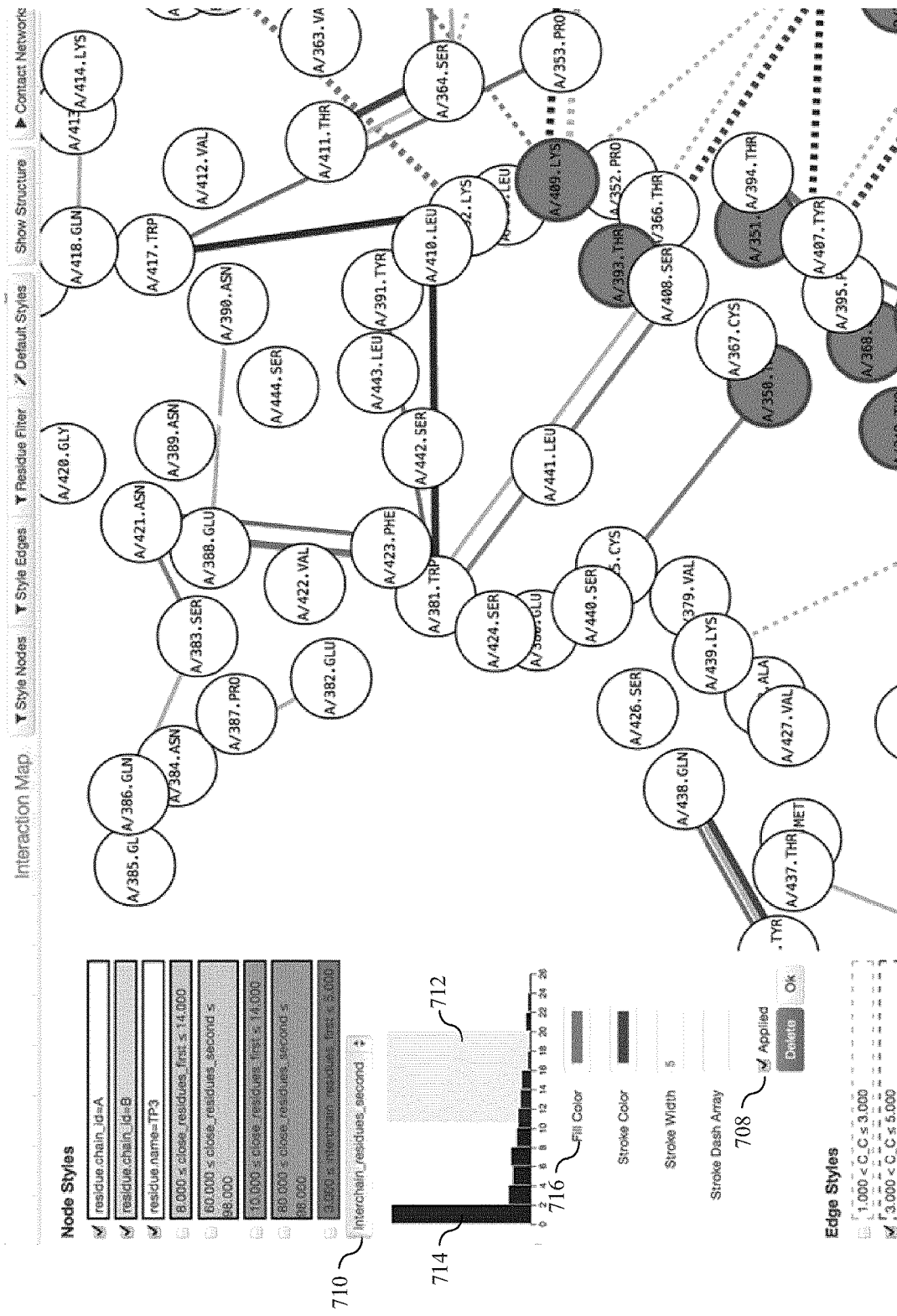

In some embodiments, each respective node in the plurality of nodes has a value for a property associated with the corresponding particle $p_i$ in $\{p_1, \ldots, p_N\}$ represented by the respective node and a subset of the plurality of nodes is conditionally graphically highlighted as a function of the value of property associated with the respective particles $p_i$ in $\{p_1, \ldots, p_N\}$ corresponding to the plurality of nodes. In one example, referring to FIG. 8, when the applied toggle 708 is checked, those nodes that satisfy the "interchain_residues_second" 710 property by having a value for this property that is within region 712 of histogram 714 are colored by fill color 716. This illustrates how a node is not graphically highlighted when the property does not satisfy a first threshold condition and a node is graphically highlighted when the property does satisfy a first threshold condition. Moreover, this illustrates how a histogram 714 of values for the property is displayed and the threshold condition is determined by a selection (e.g., using mouse cursor functions such as drag and drop) of a subset 712 of the histogram of values. FIGS. 9 and 10 illustrate how the nodes change their highlighting shade as different subsets 712 of values are selected using histogram 714. In FIG. 8 through 10, a threshold condition is satisfied when a value of the property is within the subset of the histogram of values. That is, when a node has a property within subset 712, the node is graphically highlighted. In alternative embodiments, the threshold condition is satisfied when a value of the property for the node is outside the subset of the histogram values. In such alternative embodiments, the nodes that have values for the property represented by the histogram 714 that are outside subset 712 are in fact that ones that are graphically highlighted.

Figure 11:
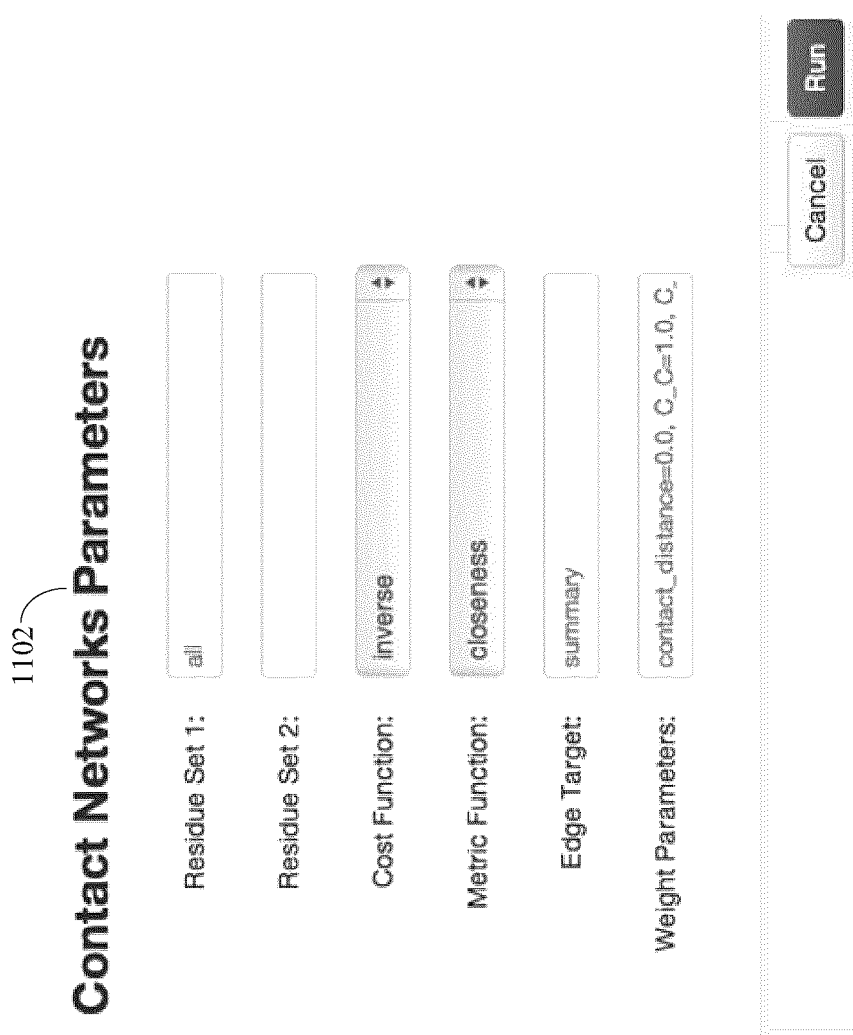
FIG. 11 illustrates the graphical user interface of FIG. 7 in which the plotting (D) conditionally plots a subset of the plurality of nodes as a function of the one or more properties associated with the respective particles $p_i$ in $\{p_1, \ldots, p_N\}$ corresponding to the plurality of nodes and in which a property of one or more of the nodes in the plurality of nodes is determined by launching a computational module directly inline within the graphical user interface in accordance with the systems and methods of the present disclosure.

Referring to FIG. 11, each respective node in the plurality of nodes is associated with one or more properties associated with the respective particle $p_i$ in $\{p_1, \ldots, p_N\}$ represented by the respective node and nodes are conditionally graphically highlighted as a function of the one or more properties associated with the respective particles $p_i$ in $\{p_1, \ldots, p_N\}$ corresponding to the plurality of nodes and a property of one or more of the nodes in the plurality of nodes is determined by launching a computational module using a form 1102 directly inline within the graphical user interface.

Figure 12:
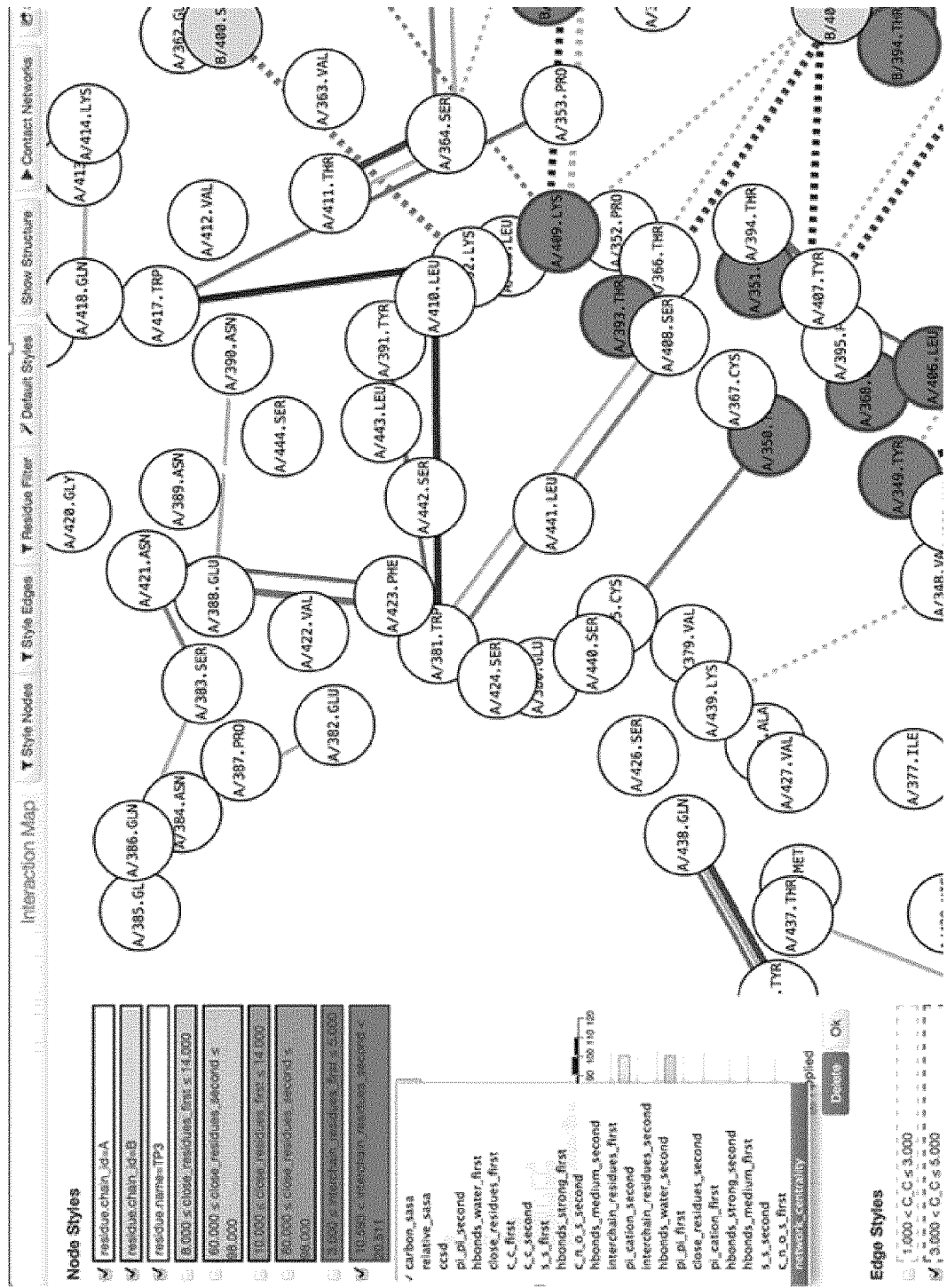
FIG. 12 illustrates selection of the property of the nodes computed by the computation module launched inline by the interface of FIG. 11 in accordance with the systems and methods of the present disclosure.
Figure 13:
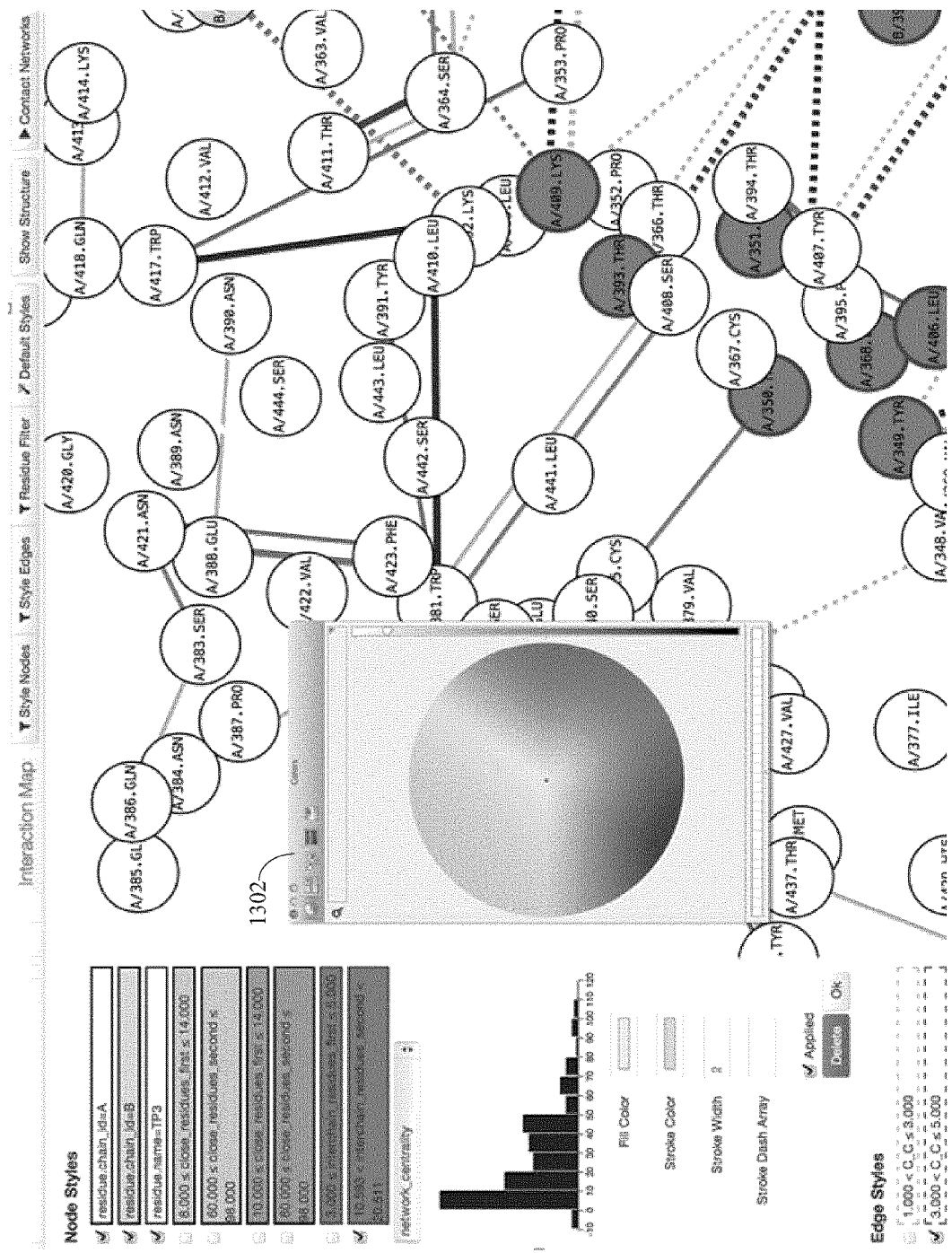
FIG. 13 illustrates the defining of a node style for the property of the nodes computed by the computation module launched inline by the interface of FIG. 11 in accordance with the systems and methods of the present disclosure.

FIG. 12 illustrates selection of the property "network centrality" of the nodes computed by the computation module launched inline by the form 1102 of FIG. 11 in accordance with the systems and methods of the present disclosure. FIG. 13 illustrates the defining of a node style using interface 1302 for the property of the nodes computed by the computation module launched inline by the interface of FIG. 11 in accordance with the systems and methods of the present disclosure.

Figure 14:
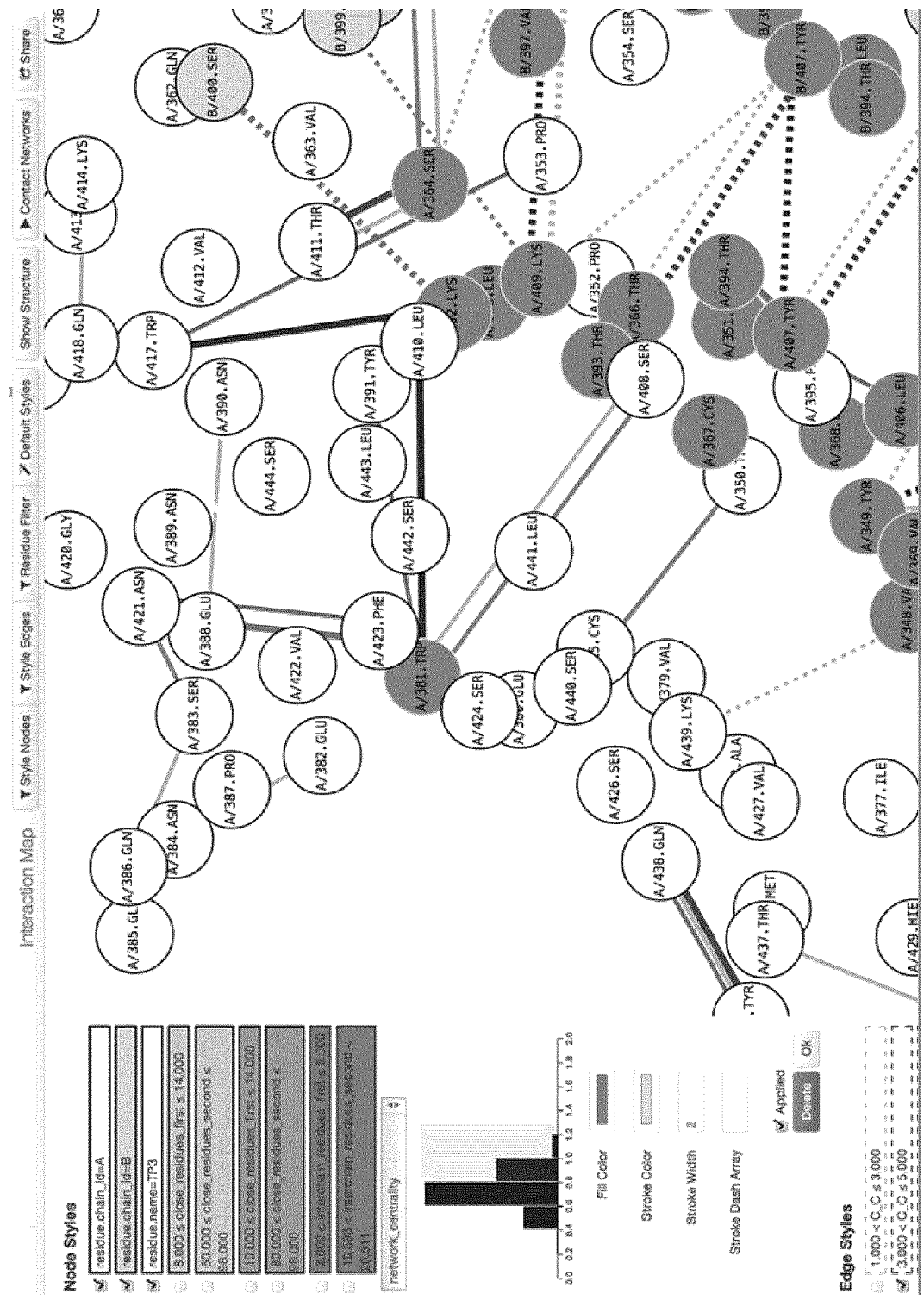
FIG. 14 illustrates the graphical user interface of FIG. 13 in which the property of the nodes computed by the computation module launched inline by the interface of FIG. 11 is displayed as a histogram of values for the purpose of determining which nodes of the plurality are to be displayed by user selection of a subset of the histogram in accordance with the systems and methods of the present disclosure.

FIG. 14 illustrates the graphical user interface of FIG. 13 in which the property of the nodes computed by the computation module launched inline by the interface of FIG. 11 is displayed as a histogram of values 1402 for the purpose of determining which nodes of the plurality are to be displayed by user selection of a subset of the histogram in accordance with the systems and methods of the present disclosure.

Figure 15:
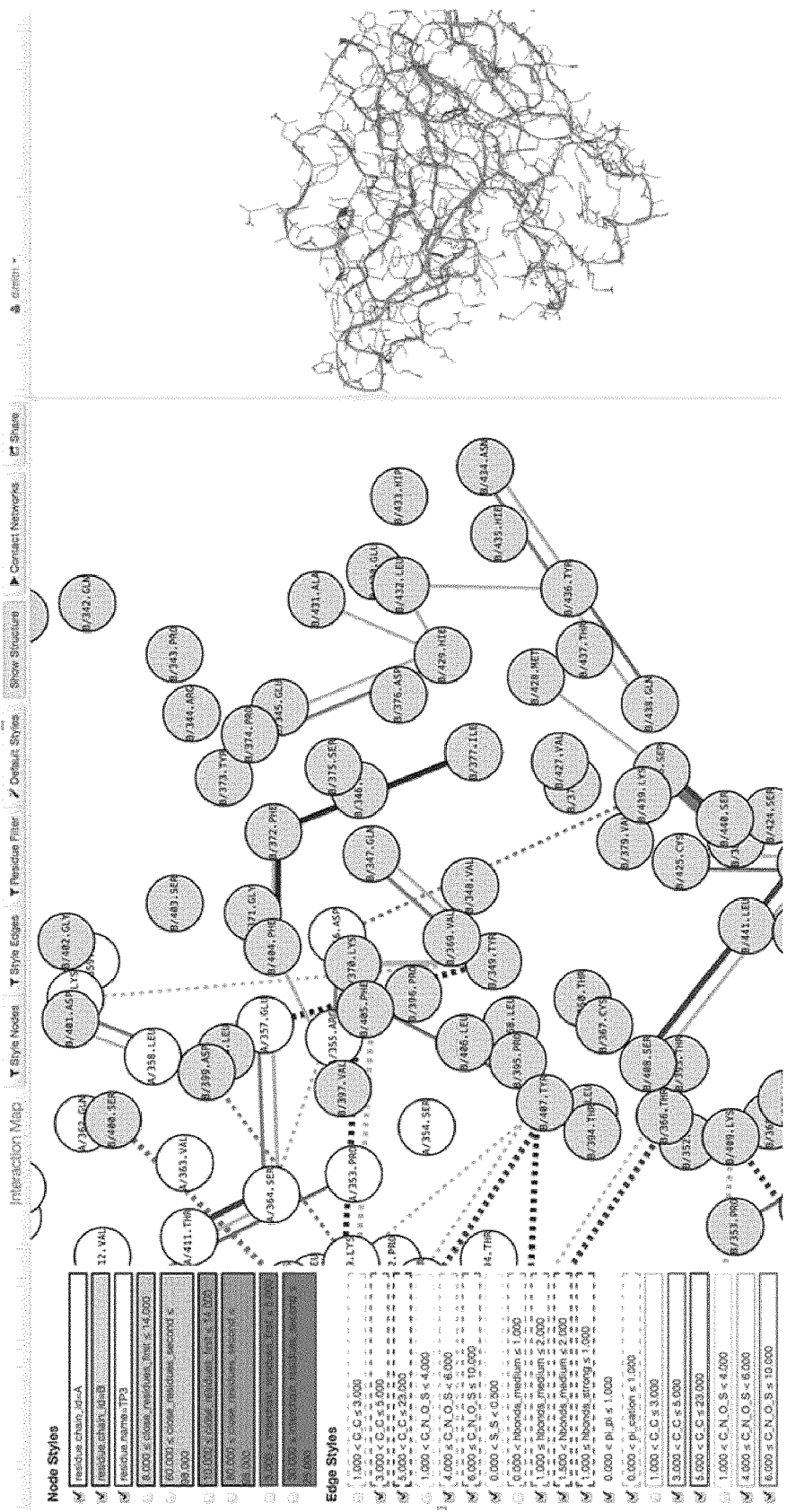
FIG. 15 provides another view of the graphical user interface of FIG. 7 in which the plurality of nodes can be zoomed by user action so that a subset of the plurality of nodes is displayed, and in which a subset of the N three-dimensional coordinates $\{x_1, \ldots, x_N\}$ corresponding to the subset of the plurality of nodes is displayed along with the plurality of nodes in a side by side fashion in accordance with the systems and methods of the present disclosure.

FIG. 15 provides another view of the graphical user interface of FIG. 7 in which the plurality of nodes can be zoomed by user action so that a subset of the plurality of nodes is displayed, and in which a subset of the N three-dimensional coordinates $\{x_1, \ldots, x_N\}$ corresponding to the subset of the plurality of nodes is displayed along with the plurality of nodes in a side by side fashion in accordance with the systems and methods of the present disclosure. The plurality of nodes can be zoomed by user action so that a subset of the plurality of nodes is displayed. Moreover, upon receiving instructions to display a subset of the N three-dimensional coordinates $\{x_1, \ldots, x_N\}$ corresponding to the subset of the plurality of nodes in a side by side fashion. In some embodiments, the subset of the plurality of nodes and the subset of the N three-dimensional coordinates $\{x_1, \ldots, x_N\}$ can be rotated, translated and zoomed in three dimensional space in a concerted fashion. In alternative embodiments, the subset of the plurality of nodes and the subset of the N three-dimensional coordinates $\{x_1, \ldots, x_N\}$ can be rotated, translated and zoomed in three dimensional space independently of each other.

Figure 16:
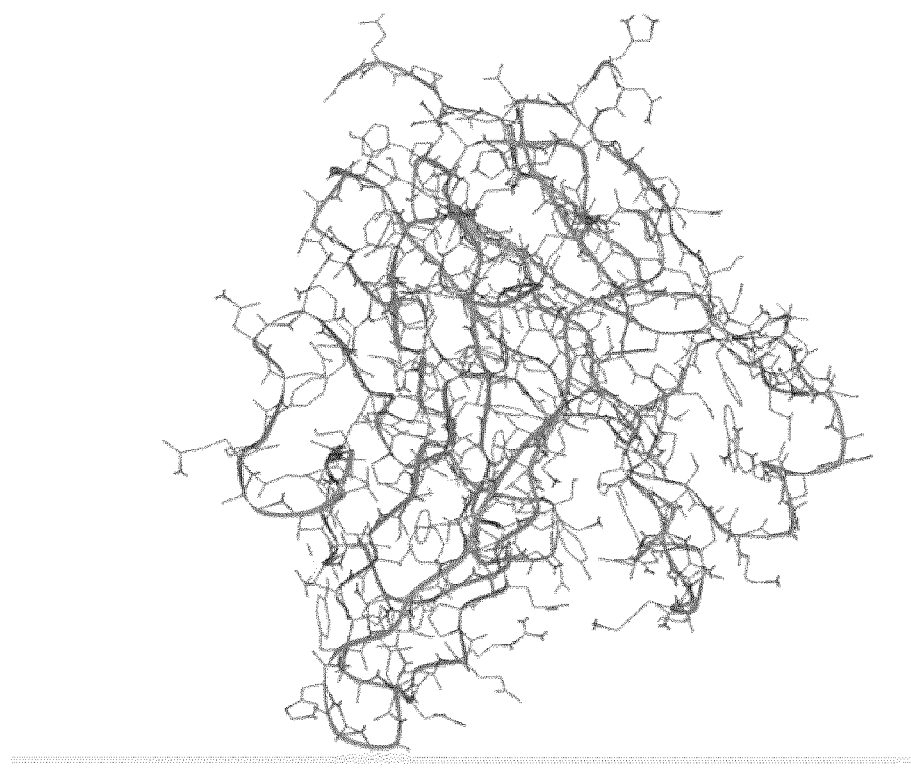
FIG. 16 illustrates a closer up view of the graphical user interface of FIG. 15 in which the plurality of nodes can be zoomed by user action so that a subset of the plurality of nodes is displayed, and in which a subset of the N three-dimensional coordinates $\{x_1, \ldots, x_N\}$ corresponding to the subset of the plurality of nodes is displayed along with the plurality of nodes in a side by side fashion in accordance with the systems and methods of the present disclosure.
Figure 16:
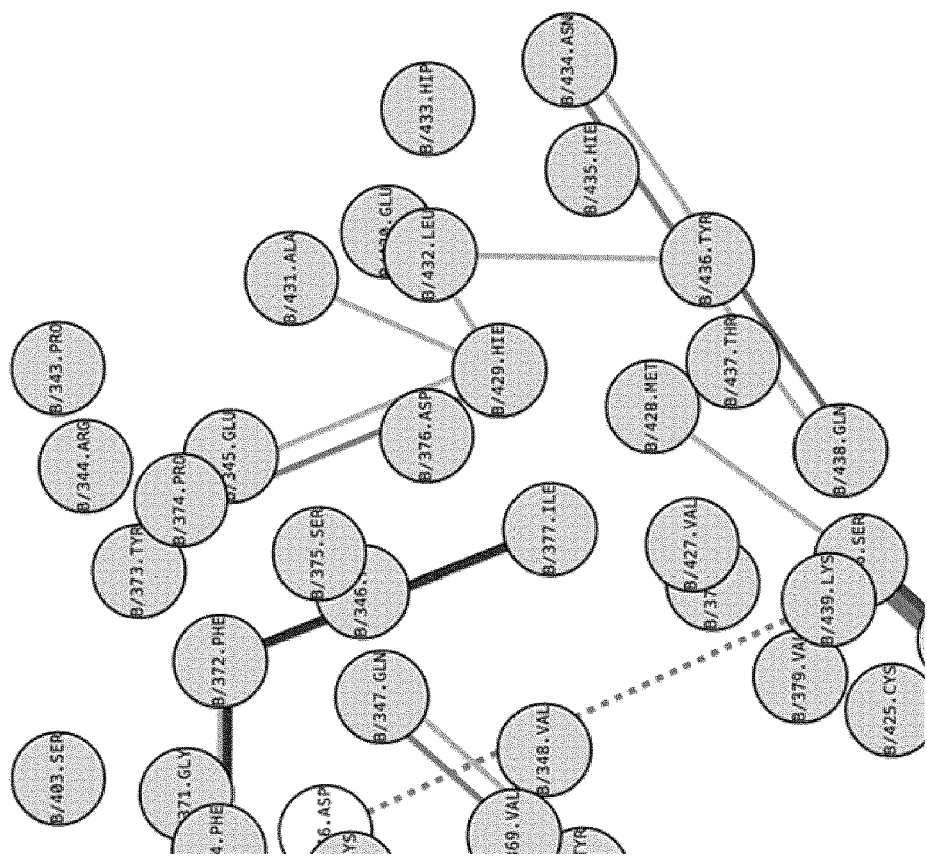

FIG. 16 illustrates a closer up view of the graphical user interface of FIG. 15 in which the plurality of nodes can be zoomed by user action so that a subset of the plurality of nodes is displayed, and in which a subset of the N three-dimensional coordinates $\{x_1, \ldots, x_N\}$ corresponding to the subset of the plurality of nodes is displayed along with the plurality of nodes in a side by side fashion in accordance with the systems and methods of the present disclosure.

Figure 17:
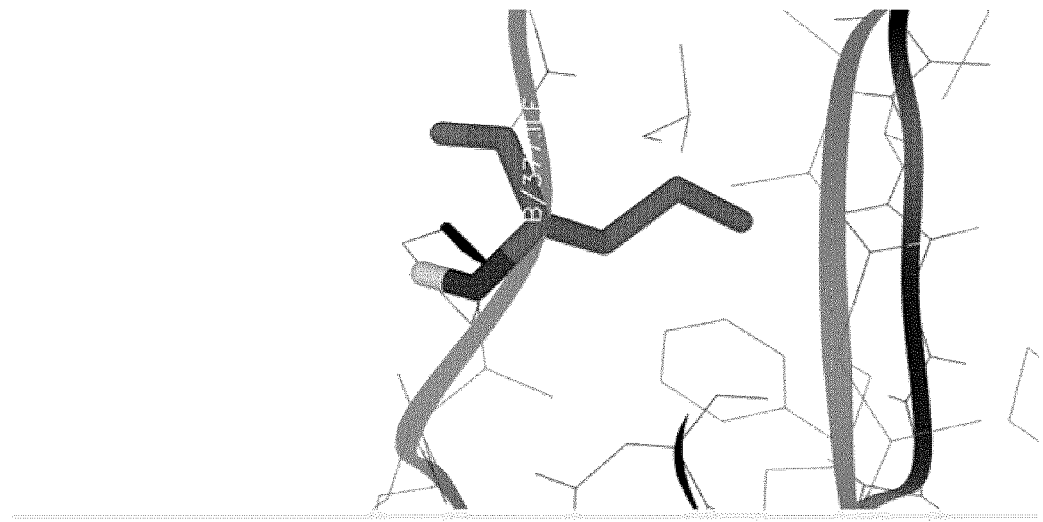
FIG. 17 illustrates the graphical user interface of FIG. 16 in which the display can be snapped to a particular residue in coordinated fashion in both panels in accordance with the systems and methods of the present disclosure.
Figure 17:
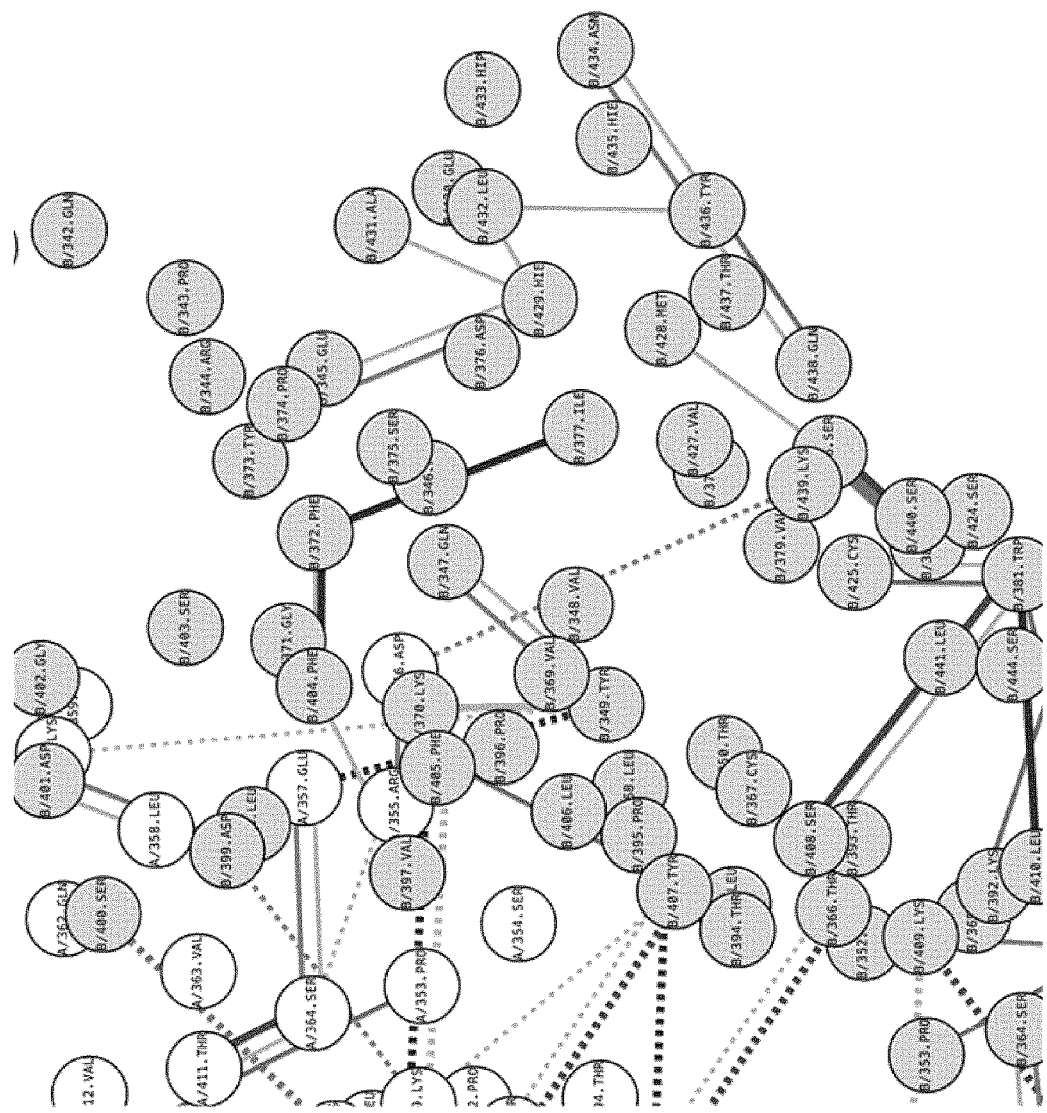

FIG. 17 illustrates the graphical user interface of FIG. 16 in which the display can be snapped to a particular residue in coordinated fashion in both panels in accordance with the systems and methods of the present disclosure.

The methods illustrated in FIG. 2 may be governed by instructions that are stored in a computer readable storage medium and that are executed by at least one processor of at least one server. Each of the operations shown in FIG. 2 may correspond to instructions stored in a non-transitory computer memory or computer readable storage medium. In various implementations, the non-transitory computer readable storage medium includes a magnetic or optical disk storage device, solid state storage devices such as Flash memory, or other non-volatile memory device or devices. The computer readable instructions stored on the non-transitory computer readable storage medium may be in source code, assembly language code, object code, or other instruction format that is interpreted and/or executable by one or more processors.

Plural instances may be provided for components, operations or structures described herein as a single instance. Finally, boundaries between various components, operations, and data stores are somewhat arbitrary, and particular operations are illustrated in the context of specific illustrative configurations. Other allocations of functionality are envisioned and may fall within the scope of the implementation(s). In general, structures and functionality presented as separate components in the exemplary configurations may be implemented as a combined structure or component. Similarly, structures and functionality presented as a single component may be implemented as separate components. These and other variations, modifications, additions, and improvements fall within the scope of the implementation (s).

It will also be understood that, although the terms "first," "second," etc. may be used herein to describe various elements, these elements should not be limited by these terms. These terms are only used to distinguish one element from another. For example, a first contact could be termed a second contact, and, similarly, a second contact could be termed a first contact, which changing the meaning of the description, so long as all occurrences of the "first contact" are renamed consistently and all occurrences of the second contact are renamed consistently. The first contact and the second contact are both contacts, but they are not the same contact.

The terminology used herein is for the purpose of describing particular implementations only and is not intended to be limiting of the claims. As used in the description of the implementations and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises"

and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in accordance with a determination" or "in response to detecting," that a stated condition precedent is true, depending on the context. Similarly, the phrase "if it is determined (that a stated condition precedent is true)" or "if (a stated condition precedent is true)" or "when (a stated condition precedent is true)" may be construed to mean "upon determining" or "in response to determining" or "in accordance with a determination" or "upon detecting" or "in response to detecting" that the stated condition precedent is true, depending on the context.

The foregoing description included example systems, methods, techniques, instruction sequences, and computing machine program products that embody illustrative implementations. For purposes of explanation, numerous specific details were set forth in order to provide an understanding of various implementations of the inventive subject matter. It will be evident, however, to those skilled in the art that implementations of the inventive subject matter may be practiced without these specific details. In general, well-known instruction instances, protocols, structures and techniques have not been shown in detail.

The foregoing description, for purpose of explanation, has been described with reference to specific implementations. However, the illustrative discussions above are not intended to be exhaustive or to limit the implementations to the precise forms disclosed. Many modifications and variations are possible in view of the above teachings. The implementations were chosen and described in order to best explain the principles and their practical applications, to thereby enable others skilled in the art to best utilize the implementations and various implementations with various modifications as are suited to the particular use contemplated.

What is claimed is:

1. A computer-implemented method for visualizing physical properties of a molecule in two dimensions, wherein the molecule comprises a set of $\{p_1, \ldots, p_N\}$ particles, each particle $p_i$ in the set of particles representing a different plurality of covalently bound atoms in the molecule, the method performed on a first computer system having at least one processor and memory storing at least one program for execution by the at least one processor to perform the method, comprising:

(A) obtaining a set of N three-dimensional coordinates $\{x_1, \ldots, x_N\}$ by x-ray crystallography, nuclear magnetic resonance spectroscopic techniques, electron microscopy, modeling or from a non-transitory computer readable storage medium, wherein each respective $x_i$ in $\{x_1, \ldots, x_N\}$ corresponds to a $p_i$ in $\{p_1, \ldots, p_N\}$ and represents the position of $p_i$ in three-dimensional space, wherein N is a positive integer of greater than 30;

(B) minimizing a cost function containing an error in a set of two-dimensional coordinates corresponding to the set of N three-dimensional coordinates using a minimization function module:

$$E(c_1, c_2, \ldots, c_N) = \sum_{i<j}^{N} w_{ij}|\delta_{ij} - D(c_i, c_j)|^2$$

using the set of N three-dimensional coordinates wherein,
i and j are integers greater than zero,
$\delta_{ij}$ is a distance between a pair of three-dimensional coordinates $x_i$ and $x_j$ in $\{x_1, \ldots, x_N\}$,
$E(c_1, c_2, \ldots, c_N)$ is an error in the set of two-dimensional coordinates $(c_1, c_N)$, wherein each two-dimensional coordinate $c_i$ in $(c_1, c_N)$ uniquely corresponds to a three-dimensional coordinate $x_i$ in $\{x_1, \ldots, x_N\}$ so that each respective $p_i$ in $\{p_1, \ldots, p_N\}$ is represented by a three-dimensional coordinate $x_i$ in $\{x_1, \ldots, x_N\}$ and a corresponding two-dimensional coordinate $c_i$ in $(c_1, \ldots, c_N)$,
$D(c_i, c_j)$ is a distance between the two-dimensional coordinates $c_i$ and $c_j$ in $(c_1, \ldots, c_N)$, and
$w_{ij}$ is a weight for the two-dimensional pair $(p_i, p_j)$ in a matrix of weights, wherein the matrix of weights has a weight for each two-dimensional pair $(p_i, p_j)$ in $(p_1, \ldots, p_N)$,
wherein the minimizing alters the values of coordinates of the set of two-dimensional coordinates $(c_1, \ldots, c_N)$ using a refinement algorithm until an exit condition is achieved;

(C) obtaining a plurality of sets of physical properties $S_{Mk}$ from a non-transitory computer readable storage medium, each physical property $s_{i,j}$ in $S_{Mk}$ representing a respective physical property k shared by a pair of particles $(p_i, p_j)$ in $\{p_1, \ldots, p_N\}$ in the molecule;

(D) plotting $(c_1, \ldots, c_N)$, with a graphical user interface, after the exit condition is achieved, as a plurality of nodes of a two-dimensional graph; and (E) plotting, with the graphical user interface, a first plurality of edges for the two-dimensional graph, wherein
each respective edge in the first plurality of edges connects a two-dimensional coordinate pair $(c_i, c_j)$ in the graph that corresponds to a pair of particles $(p_i, p_j)$ in $\{p_1, \ldots, p_N\}$, and
a first characteristic of each respective edge in the first plurality of edges is determined by a respective physical property $s_{i,j}$ in $S_{M1}$ for the pair of particles $(p_i, p_j)$ in $\{p_1, \ldots, p_N\}$ corresponding to the two-dimensional coordinate pair $(c_i, c_j)$ that is connected by the respective edge.

2. The computer-implemented method of claim 1 wherein k is a positive integer of 2 or greater.

3. The computer-implemented method of claim 1 wherein the plotting (E) is done on a conditional basis in which each respective edge in the first plurality of edges is conditionally plotted as a function of the respective physical property $s_{i,j}$ in $S_{M1}$ for the pair of particles $(p_i, p_j)$ in $\{p_1, \ldots, p_N\}$ corresponding to the two-dimensional coordinate pair $(c_i, c_j)$ that is connected by the respective edge.

4. The computer-implemented method of claim 3, wherein:
a first edge in the first plurality of edges is not plotted by the plotting (E) when the physical property $s_{i,j}$ does not satisfy a first threshold condition, and
the first edge is plotted by the plotting (E) when the physical property $s_{i,j}$ satisfies the first threshold condition.

5. The computer-implemented method of claim 4, wherein a histogram of values for the physical property $s_{i,j}$ of $S_{M1}$ are displayed and the first threshold condition is determined by a selection of a subset of the histogram of values.

6. The computer-implemented method of claim 5, wherein the first threshold condition is satisfied when a value of the physical property $s_{i,j}$ is outside the subset of the histogram values.

7. The computer-implemented method of claim 5, wherein the first threshold condition is satisfied when a value of the physical property $s_{i,j}$ is within the subset of the histogram of values.

8. The computer-implemented method of claim 5, wherein the subset of the histogram values is user adjustable using mouse cursor functions.

9. The computer-implemented method of claim 1, wherein the plotting (E) further comprises:
plotting a second plurality of edges for the two-dimensional graph, wherein
each respective edge in the second plurality of edges connects a two-dimensional coordinate pair $(c_i, c_j)$ in the graph that corresponds to a pair of particles $(p_i, p_j)$ in $\{p_1, \ldots, p_N\}$, and
a first characteristic of each respective edge in the second plurality of edges is determined by a respective physical property $s_{i,j}$ in $S_{M2}$ for the pair of particles $(p_i, p_j)$ in $\{p_1, \ldots, p_N\}$ corresponding to the two-dimensional coordinate pair $(c_i, c_j)$ that is connected by the respective edge.

10. The computer-implemented method of claim 9, wherein the plotting (E) further comprises:
plotting a third plurality of edges for the two-dimensional graph, wherein
each respective edge in the third plurality of edges connects a two-dimensional coordinate pair $(c_i, c_j)$ in the graph that corresponds to a pair of particles $(p_i, p_j)$ in $\{p_1, \ldots, p_N\}$, and
a first characteristic of each respective edge in the third plurality of edges is determined by a respective physical property $s_{i,j}$ in $S_{M3}$ for the pair of particles $(p_i, p_j)$ in $\{p_1, \ldots, p_N\}$ corresponding to the two-dimensional coordinate pair $(c_i, c_j)$ that is connected by the respective edge.

11. The computer-implemented method of claim 10, wherein the user is able to individually toggle on or off the display of the first plurality of edges, the second plurality of edges, and the third plurality of edges.

12. The computer-implemented method of claim 10, wherein
each edge in the first plurality of edges is plotted with a first edge style,
each edge in the second plurality of edges is plotted with a second edge style, and
each edge in the third plurality of edges is plotted with a third edge style.

13. The computer-implemented method of claim 1, wherein each respective node in the plurality of nodes is associated with one or more properties associated with the respective particle $p_i$ in $\{p_1, \ldots, p_N\}$ represented by the respective node and wherein the plotting (D) conditionally, graphically highlights a subset of the plurality of nodes as a function of the one or more properties associated with the respective particles $p_i$ in $\{p_1, \ldots, p_N\}$ corresponding to the plurality of nodes.

14. The computer-implemented method of claim 1, wherein each particle in a first subset of the particles $p_i$ in $\{p_1, \ldots, p_N\}$ has a first property and each particle in second subset of the particles $p_i$ in $\{p_1, \ldots, p_N\}$ does not have the first property, and
the plotting (D) comprises plotting the nodes in the plurality of nodes corresponding to the first subset of the particles and not plotting the nodes in the plurality of nodes corresponding to the second subset of the particles.

15. The computer-implemented method of claim 14, wherein the user is able to individually toggle on or off the display of (i) the nodes in the plurality of nodes corresponding to the first subset of the particles and (ii) the nodes in the plurality of nodes corresponding to the second subset of the particles.

16. The computer-implemented method of claim 1, wherein
each particle in a first subset of the particles $p_i$ in $\{p_1, \ldots, p_N\}$ has a first property and each particle in a second subset of the particles $p_i$ in $\{p_1, \ldots, p_N\}$ does not have the first property and
the plotting (D) comprises plotting the nodes in the plurality of nodes corresponding to the first subset of the particles with a first graphic attribute and plotting the nodes in the plurality of nodes corresponding to the second subset of the particles with a second graphic attribute.

17. The computer-implemented method of claim 16, wherein the first graphic attribute is a first color and the second graphic attribute is a second color.

18. The computer-implemented method of claim 1, wherein the method further comprises providing a graphical user interface that performs the plotting (D) and the plotting (E), wherein
each respective node in the plurality of nodes is associated with one or more properties associated with the respective particle $p_i$ in $\{p_1, \ldots, p_N\}$ represented by the respective node,
the plotting (D) conditionally, graphically highlights a subset of the plurality of nodes as a function of the one or more properties associated with the respective particles $p_i$ in $\{p_1, \ldots, p_N\}$ corresponding to the plurality of nodes, and
a property of one or more of the nodes in the plurality of nodes is determined by launching a computational module directly inline within the graphical user interface.

19. The computer-implemented method of claim 1, wherein
each respective node in the plurality of nodes has a value for a property associated with the corresponding particle $p_i$ in $\{p_1, \ldots, p_N\}$ represented by the respective node, and
the plotting (D) conditionally graphically highlights a subset of the plurality of nodes as a function of the value of property associated with the respective particles $p_i$ in $\{p_1, \ldots, p_N\}$ corresponding to the plurality of nodes.

20. The computer-implemented method of claim 19, wherein
a node is not graphically highlighted by the plotting (D) when the property does not satisfy a first threshold condition, and
a node is graphically highlighted by the plotting (D) when the property does satisfy a first threshold condition.

21. The computer-implemented method of claim 20, wherein a histogram of values for the property is displayed and the first threshold condition is determined by a selection of a subset of the histogram of values.

22. The computer-implemented method of claim 21, wherein the first threshold condition is satisfied when a value of the property is outside the subset of the histogram values.

23. The computer-implemented method of claim 21, wherein the first threshold condition is satisfied when a value of the property is within the subset of the histogram of values.

24. The computer-implemented method of claim 21, wherein the subset of the histogram values is user adjustable using mouse cursor functions.

25. The computer-implemented method of claim 1 the obtaining (C) is performed by launching a computational module directly inline within the graphical user interface that computes a set of physical properties in the one or more sets of physical properties SM.

26. The computer-implemented method of claim 1, wherein the plurality of nodes can be zoomed by user action so that a subset of the plurality of nodes is displayed, and wherein, the method further comprises receiving instructions to display all or a subset of the N three-dimensional coordinates $\{x_1, \ldots, x_N\}$ in a side by side fashion to all or a portion of the plurality of nodes.

27. The computer-implemented method of claim 26, wherein the plurality of nodes and the N three-dimensional coordinates $\{x_1, \ldots, x_N\}$ can be rotated, translated and zoomed in three dimensional space in a concerted fashion.

28. The computer-implemented method of claim 26, wherein the plurality of nodes and the N three-dimensional coordinates $\{x_1, \ldots, x_N\}$ can be rotated, translated and zoomed in three dimensional space independently of each other.

29. A computer system for visualizing physical properties of a molecule in two dimensions, wherein the molecule comprises the set of $\{p_1, \ldots, p_N\}$ particles, each particle $p_i$ in the set of particles representing a different plurality of covalently bound atoms in the molecule, the computer system comprising at least one processor and memory storing at least one program for execution by the at least one processor, the memory further comprising instructions for:
(A) obtaining a set of N three-dimensional coordinates $\{x_1, \ldots, x_N\}$ by x-ray crystallography, nuclear magnetic resonance spectroscopic techniques, electron microscopy, modeling or from a non-transitory computer readable storage medium, wherein each respective $x_i$ in $\{x_1, \ldots, x_N\}$ corresponds to a $p_i$ in $\{p_1, \ldots, p_N\}$ and represents the position of $p_i$ in three-dimensional space, wherein N is a positive integer of greater than 30;
(B) minimizing a cost function containing an error in a set of two-dimensional coordinates corresponding to the set of N three-dimensional coordinates using a minimization function module:

$$E(c_1, c_2, \ldots, c_N) = \sum_{i<j}^{N} w_{ij}|\delta_{ij} - D(c_i, c_j)|^2$$

using the set of N three-dimensional coordinates wherein,
i and j are integers greater than zero,
$\delta_{ij}$ is a distance between a pair of three-dimensional coordinates $x_i$ and $x_j$ in $\{x_1, \ldots, x_N\}$, $E(c_1, c_2, \ldots, c_N)$ is an error in the set of two-dimensional coordinates $(c_1, \ldots, c_N)$, wherein each two-dimensional coordinate $c_i$ in $(c_1, \ldots, c_N)$ uniquely corresponds to a three-dimensional coordinate $x_i$ in $\{x_1, \ldots, x_N\}$ so that each respective $p_i$ in $\{p_1, \ldots, p_N\}$ is represented by a three-dimensional coordinate $x_i$ in $\{x_1, \ldots, x_N\}$ and a corresponding two-dimensional coordinate $c_i$ in $(c_1, \ldots, c_N)$,
$D(c_i, c_j)$ is a distance between the two-dimensional coordinates $c_i$ and $c_j$ in $(c_1, \ldots, c_N)$, and
$w_{ij}$ is a weight for the two-dimensional pair $(p_i, p_j)$ in a matrix of weights, wherein the matrix of weights has a weight for each two-dimensional pair $(p_i, p_j)$ in $(p_1, \ldots, p_N)$,
wherein the minimizing alters the values of coordinates of the set of two-dimensional coordinates $(c_1, \ldots, c_N)$ using a refinement algorithm until an exit condition is achieved;
(C) obtaining a plurality of sets of physical properties $S_{Mk}$ from a non-transitory computer readable storage medium, each physical property $s_{i,j}$ in $S_{Mk}$ representing a respective physical property k shared by a pair of particles $(p_i, p_j)$ in $\{p_1, \ldots, p_N\}$ in the molecule;
(D) plotting $(c_1, \ldots, c_N)$, with a graphical user interface, after the exit condition is achieved, as a plurality of nodes of a two-dimensional graph; and
(E) plotting, with the graphical user interface, a first plurality of edges for the two-dimensional graph, wherein
each respective edge in the first plurality of edges connects a two-dimensional coordinate pair $(c_i, c_j)$ in the graph that corresponds to a pair of particles $(p_i, p_j)$ in $\{p_1, \ldots, p_N\}$, and
a first characteristic of each respective edge in the first plurality of edges is determined by a respective physical property $s_{i,j}$ in $S_{M1}$ for the pair of particles $(p_i, p_j)$ in $\{p_1, \ldots, p_N\}$ corresponding to the two-dimensional coordinate pair $(c_i, c_j)$ that is connected by the respective edge.

30. A non-transitory computer readable storage medium storing a visualization module for visualizing physical properties of a molecule in two dimensions, wherein the molecule comprises the set of $\{p_1, \ldots, p_N\}$ particles, each particle $p_i$ in the set of particles representing a different plurality of covalently bound atoms in the molecule, the visualization module comprising instructions for:
(A) obtaining a set of N three-dimensional coordinates $\{x_1, \ldots, x_N\}$ by x-ray crystallography, nuclear magnetic resonance spectroscopic techniques, electron microscopy, modeling or from a non-transitory computer readable storage medium, wherein each respective $x_i$ in $\{x_1, \ldots, x_N\}$ corresponds to a $p_i$ in $\{p_1, \ldots, p_N\}$ and represents the position of $p_i$ in three-dimensional space, wherein N is a positive integer of greater than 30;
(B) minimizing a cost function containing an error in a set of two-dimensional coordinates corresponding to the set of N three-dimensional coordinates using a minimization function module:

$$E(c_1, c_2, \ldots, c_N) = \sum_{i<j}^{N} w_{ij}|\delta_{ij} - D(c_i, c_j)|^2$$

using the set of N three-dimensional coordinates wherein, i and j are integers greater than zero, $\delta_{ij}$ is a distance between a pair of three-dimensional coordinates $x_i$ and $x_j$ in $\{x_1, \ldots, x_N\}$, $E(c_1, c_2, \ldots, C_N)$ is an error in the set of two-dimensional coordinates $(c_1, \ldots, c_N)$, wherein each two-dimensional coordinate $c_i$ in $(c_1, \ldots, c_N)$ uniquely corresponds to a three-dimensional coordinate $x_i$ in $\{x_1, \ldots, x_N\}$ so that each respective $p_i$ in $\{p_1, \ldots, p_N\}$ is represented by a three-dimensional coordinate $x_i$ in $\{x_1, \ldots, x_N\}$ and a corresponding two-dimensional coordinate $c_i$ in $(c_1, \ldots, c_N)$, $D(c_i, c_j)$ is a distance between the two-dimensional coordinates $c_i$ and $c_j$ in $(c_1, \ldots, c_N)$, and $w_{ij}$ is a weight for the two-dimensional pair $(p_i, p_j)$ in a matrix of weights, wherein the matrix of weights has a weight for each two-dimensional pair $(p_i, p_j)$ in $(p_1, \ldots, p_N)$, wherein the minimizing alters the values of coordinates of the set of two-dimensional coordinates $(c_1, \ldots, c_N)$ using a refinement algorithm until an exit condition is achieved;

(C) obtaining a plurality of sets of physical properties $S_{Mk}$ from a non-transitory computer readable storage medium, each physical property $s_{i,j}$ in $S_{Mk}$ representing a respective physical property k shared by a pair of particles $(p_i, p_j)$ in $\{p_1, \ldots, p_N\}$ in the molecule;

(D) plotting $(c_1, \ldots, c_N)$, with a graphical user interface, after the exit condition is achieved, as a plurality of nodes of a two-dimensional graph; and (E) plotting, with the graphical user interface, a first plurality of edges for the two-dimensional graph, wherein each respective edge in the first plurality of edges connects a two-dimensional coordinate pair $(c_i, c_j)$ in the graph that corresponds to a pair of particles $(p_i, p_j)$ in $\{p_1, \ldots, p_N\}$, and a first characteristic of each respective edge in the first plurality of edges is determined by a respective physical property $s_{i,j}$ in $S_{M1}$ for the pair of particles $(p_i, p_j)$ in $\{p_1, \ldots, p_N\}$ corresponding to the two-dimensional coordinate pair $(c_i, c_j)$ that is connected by the respective edge.

\* \* \* \* \*